(12) United States Patent
Xu et al.

(10) Patent No.: US 7,943,303 B2
(45) Date of Patent: May 17, 2011

(54) METHOD FOR ENGINEERING STRAND-SPECIFIC NICKING ENDONUCLEASES FROM RESTRICTION ENDONUCLEASES

(75) Inventors: Shuang-yong Xu, Lexington, MA (US); James Samuelson, Newburyport, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 11/013,260

(22) Filed: Dec. 15, 2004

(65) Prior Publication Data
US 2005/0158834 A1    Jul. 21, 2005

Related U.S. Application Data

(60) Provisional application No. 60/530,754, filed on Dec. 18, 2003.

(51) Int. Cl.
*C12Q 1/00* (2006.01)
*C12N 15/00* (2006.01)
*C12N 15/09* (2006.01)
*C12N 15/11* (2006.01)
*C12N 15/52* (2006.01)

(52) U.S. Cl. ......... 435/6; 435/320.1; 435/471; 435/478; 536/23.1; 536/23.2; 536/24.1

(58) Field of Classification Search .................. None
See application file for complete search history.

(56) References Cited

U.S. PATENT DOCUMENTS

| | | | |
|---|---|---|---|
| 6,395,523 B1 | 5/2002 | Kong et al. | |
| 6,660,475 B2 | 12/2003 | Jack et al. | |
| 2003/0022317 A1* | 1/2003 | Jack et al. | 435/91.1 |
| 2003/0100094 A1 | 5/2003 | Heiter et al. | |

FOREIGN PATENT DOCUMENTS
EP    1176204 A1    1/2002

OTHER PUBLICATIONS

Abdurashitov et al., Mol. Biol. (Mosk) 30: 1261-1267 (1996).
Arkin et al., Proc. Natl. Acad. Sci. USA 89: 7811-7815 (1992).
Arnold, Curr. Opin. Biotechnol. 4: 450-455 (1993).
Besnier et al., H. EMBO Report 2: 782-786 (2001).
Cadwell et al., PCR Methods Applic. 2: 28-33 (1992).
Delagrave et al., Biotechnology Res. 11: 1548-1552 (1993).
Dorner et al., J. Mol. Biol. 285: 1515-1523 (1999).
Geider et al., J. Biol. Chem. 257: 6488-6493 (1982).
Heitman et al., Proteins 7: 185-197 (1990).
Heitman et al., EMBO J. 9:3369-3378 (1990).
Higashitani et al., J. Mol. Biol. 237: 388-400 (1994).
Leung et al., Technique 1: 11-15 (1989).
Long-McGie et al., Biotechnol. Bioeng. 68: 121-125 (2000).
Morgan et al., Biol. Chem. 381: 1123-1125 (2000).
Morrison et al., Biotechniques 14: 454-457 (1993).
Roberts et al., Nucl. Acids Res. 31: 1805-1812 (2003).
Sambrook et al., Molecular Cloning: A Laboratory Manual, $2^{nd}$ ed. Pub. Cold Spring Harbor Laboratory, Cold Spring, NY, 15.105-15.107 (1989).
Stahl et al., Proc. Natl. Acad. Sci. USA 93: 6175-6180 (1996).
Stemmer, Proc. Natl. Acad. Sci. USA 91: 10747-10751 (1994).
Wayne et al., Gene 195: 321-328 (1997).
Xia et al., Nucl. Acids Res. 16: 9477-9487 (1988).
Xu et al., Proc. Natl. Acad. Sci. USA 98: 12990-12995 (2001).
Zhang et al., Virology 240: 366-375 (1998).

* cited by examiner

*Primary Examiner* — Maria Marvich
(74) *Attorney, Agent, or Firm* — Harriet M. Strimpel

(57) ABSTRACT

Methods are provided for engineering novel strand-specific nicking endonucleases by means of an in vivo enrichment of a plasmid library containing a randomly mutagenized restriction endonuclease gene. The plasmids contain adjacent to the gene a cleavable or nickable sequence for cleaving or nicking by the endonuclease product of the gene and a second recognition site for a second endonuclease. The plasmid library is used to transform unmodified host cells. Plasmids from the cultured transformed cells may be analyzed by an in vitro assay for nicking and the nicked plasmids pooled and used to transform host cells. The product is then pooled and the single-stranded specificity of the endonuclease is then determined. The product is either cloned after amplification or identified by use of a selectable marker.

11 Claims, 13 Drawing Sheets

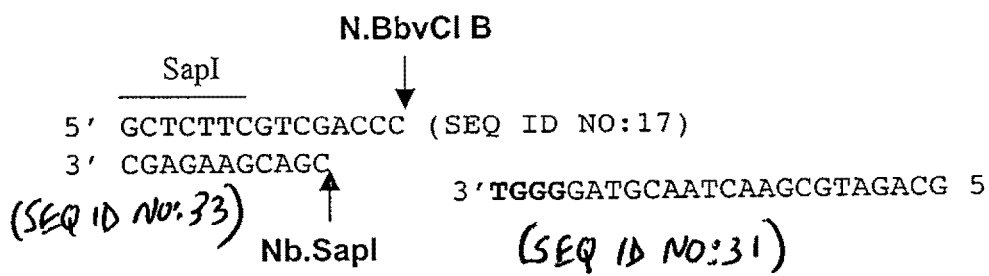
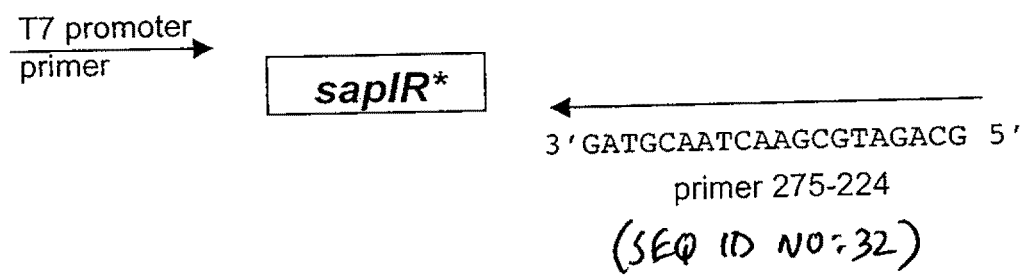
Figure 2 pUC19 substrate
5' TGCGTATTGGGCGCTCTTCCGCTTCCTCG 3'
(SEQ ID NO:19)
3' ACGCATAACCCGCGAGAAGGCGAAGGAGC 5'

Nb.SapI
Gel-purify nicked product primer →

Run-off sequence
5' TGCGTATTGGGCGCTCTTCCGCTannnnn 3'
(SEQ ID NO:20)

Nicked template
3' ACGCATAACCCGCGAGAAGGCGA 5'

Run-off sequencing from nicked bottom strand

TGCGTATTGGGCGCTCTTCCGCTANNNN

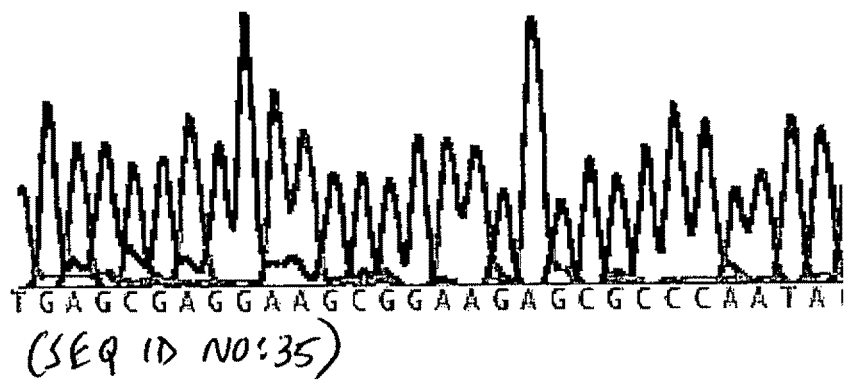

Sequencing using intact top strand as template

TGAGCGAGGAAGCGGAAGAGCGCCCAATA
(SEQ ID NO:35)

Figure 6

(SEQ ID NO:23)

```
        ATGCGGAGGCTTGCTACACAACGACGCGAGGACGCGTACAAATCAAATAGGGATTATCAG
  1     ----------+----------+----------+----------+----------+----------+  60
        M  R  R  L  A  T  Q  R  R  E  D  A  Y  K  S  N  R  D  Y  Q
        ACCGTGCACGAAGCTCAGAGCCTTCGAGTCAACTCGACCGATGATGACAACCTGAGCCTC
 61     ----------+----------+----------+----------+----------+----------+ 120
        T  V  H  E  A  Q  S  L  R  V  N  S  T  D  D  D  N  L  S  L
        TTCCTCTTGAAAGATATTTCACCCCGCGAAGATTCTAAAAATATTGTAGGATTTGGAGGC
121     ----------+----------+----------+----------+----------+----------+ 180
        F  L  L  K  D  I  S  P  R  E  D  S  K  N  I  V  G  F  G  G
        TTCGTCAAGCCCGAAATCGCCACCACCATGGCGCTTACCTTAACGACAGACATCGATAAA
181     ----------+----------+----------+----------+----------+----------+ 240
        F  V  K  P  E  I  A  T  T  M  A  L  T  L  T  T  D  I  D  K
        CAAATAAAATCAGTGCCGTTATCCTCGAATTGGAATCGGATCAGCATCGTTGCAAAGTTC
241     ----------+----------+----------+----------+----------+----------+ 300
        Q  I  K  S  V  P  L  S  S  N  W  N  R  I  S  I  V  A  K  F
        GCGAGCAACCCGTCTGTTAGCATTACTCTGGGATTTGATCAAACCCCATGGGTCGATTTC
301     ----------+----------+----------+----------+----------+----------+ 360
        A  S  N  P  S  V  S  I  T  L  G  F  D  Q  T  P  W  V  D  F
        TGGGGCATCAATTCGGACGATATCGGCCTTTCATTTGTATCGGACGCAGTCCCTCTTGAA
361     ----------+----------+----------+----------+----------+----------+ 420
        W  G  I  N  S  D  D  I  G  L  S  F  V  S  D  A  V  P  L  E
        ATGAGCATGATTGATAGCATACATATTGCCCCCGAAACACTATACCTTGATCACTCAAGC
421     ----------+----------+----------+----------+----------+----------+ 480
        M  S  M  I  D  S  I  H  I  A  P  E  T  L  Y  L  D  H  S  S
        GCATGTCTCCTTGACATTGATCCAGTGGAATCGACACGCTTCAAAACAGGCCATGGTGAC
481     ----------+----------+----------+----------+----------+----------+ 540
        A  C  L  L  D  I  D  P  V  E  S  T  R  F  K  T  G  H  G  D
        CCTTTAAGTCTGAAGAAATGCTCATACTGCGGCCGCCTTCTTCCTATAGACCTCGAGCGT
541     ----------+----------+----------+----------+----------+----------+ 600
        P  L  S  L  K  K  C  S  Y  C  G  R  L  L  P  I  D  L  E  R
        CCCGGCAAGCTGTCTTTTCACAAACATCGAGCCAAAATCACTAATCATCAGAACGAGTGT
601     ----------+----------+----------+----------+----------+----------+ 660
        P  G  K  L  S  F  H  K  H  R  A  K  I  T  N  H  Q  N  E  C
        CGTTCATGTAAGAAGTGGCGAATAAACAACTCCTTCAATCCGATGCGCACGATTGACCAG
661     ----------+----------+----------+----------+----------+----------+ 720
        R  S  C  K  K  W  R  I  N  N  S  F  N  P  M  R  T  I  D  Q
        CTTAACGAGTCAGCACTTATCACACGTGAGCGAAAGATATTCCTGCAAGAACCAGAAATT
721     ----------+----------+----------+----------+----------+----------+ 780
        L  N  E  S  A  L  I  T  R  E  R  K  I  F  L  Q  E  P  E  I
```

Figure 10-1

SEQ ID NO:23 continued)

```
     CTTCAGGAAATTAAGGATAGGACCGGCGCGGGACTTAAAAGTCAAGTGTGGGAACGATTC
781  ---------+---------+---------+---------+---------+---------+ 840
      L  Q  E  I  K  D  R  T  G  A  G  L  K  S  Q  V  W  E  R  F
     CATCGCAAGTGCTTCAACTGTAGAAAAGATCTCAAACTAAGCGAGGTTCAACTGGACCAC
841  ---------+---------+---------+---------+---------+---------+ 900
      H  R  K  C  F  N  C  R  K  D  L  K  L  S  E  V  Q  L  D  H
     ACTCGGCCGCTTGCATACCTATGGCCGATTGATGAGCATGCGACTTGCTTGTGCGCACAA
901  ---------+---------+---------+---------+---------+---------+ 960
      T  R  P  L  A  Y  L  W  P  I  D  E  H  A  T  C  L  C  A  Q
     TGCAACAATACCAAAAAAGACCGCTTTCCTGTAGATTTCTATAGCGAACAGCAGATACGC
961  ---------+---------+---------+---------+---------+---------+ 1020
      C  N  N  T  K  K  D  R  F  P  V  D  F  Y  S  E  Q  Q  I  R
     GAACTGTCGGACATTTGCGGACTTCCGTATCAGGATCTATGTGCTCGCTCGTTGAATTTA
1021 ---------+---------+---------+---------+---------+---------+ 1080
      E  L  S  D  I  C  G  L  P  Y  Q  D  L  C  A  R  S  L  N  L
     GATCAACTCGATAGGATCGAGCGTAATATCGCAGAGTTCTCCAAAGAATGGGATGTAAGA
1081 ---------+---------+---------+---------+---------+---------+ 1140
      D  Q  L  D  R  I  E  R  N  I  A  E  F  S  K  E  W  D  V  R

ACTTTCGCATCAACCGCCCGGAGAATATCGGAAGTTTACCCCGCGCGAGACCTATTTGAA
1141 ---------+---------+---------+---------+---------+---------+ 1200
      T  F  A  S  T  A  R  R  I  S  E  V  Y  P  A  R  D  L  F  E
     ACTCTTAAGAAGGAAAGCGAGTCAGCGTACAATAAAATTATTGAGAAGTTGAAGGAAAGA
1201 ---------+---------+---------+---------+---------+---------+ 1260
      T  L  K  K  E  S  E  S  A  Y  N  K  I  I  E  K  L  K  E  R
     CCAGACGCACTTCTCGATGAAGCACTACCACTGGACTGA
1261 ---------+---------+---------+---------  1299
      P  D  A  L  L  D  E  A  L  P  L  D  *
```

Figure 10-2

(SEQ ID NO:25)

```
1   MRRLATQRRE DAYKSNRDYQ TVHEAQSLRV NSTYDDNLSL FLLKDISPRE
51  DSKNIVGFGG FVKPEIATTM ALTLTTDIDK QVKSVPLSSN WNRISIVAKF
101 ASNPSVSITL GFDQTPWVDF WGINSDDIGL SFVSDAVPLE MSMIDSIHIA
151 PETLYLDHSS ACLLDIDLVE STRFKTGHGD PLSLKKCSYC GRLLPIDLER
201 PGKLSFHKHR AKITNHQNEC RSCKKWRINI SFNPMRTIDQ LNESALITRE
251 RKIFLQEPEI LQEIKDRTGA GLKSQVWERF HRKCFNCRKD LKLSEVQLDH
301 TRPLAYLWPI DEHATCLCAQ CNNTKKDRFP VDFYSEQQIR ELSDICGLPY
351 QDLCARSLNL DQLDRIERNI AEFSKEWDVR TFASTARRIS EVYPARDLFE
401 TLKKESESAY NKIIEKLKEI PDALLDEALP LD*
```

FIGURE 11

(SEQ ID NO:26)

```
  1  MRRLATQRRE  DAYKSNRDYQ  TVHEAQSLRV  NSTDDDNLSL  FLLKDISPRE
 51  DSKNIVGFGG  FVKPEIATTM  ALTLTTDIDK  QIKSVPLSSN  WNRISIVAKF
101  ASNPSVSITL  GFDQTPWVDF  WGINSDDIGL  SFVSDAVPLE  MSMIDSIHIA
151  PETLYLDHSS  ACLLDIDPVE  STRFKTGHGD  PLSLKKCSYC  GRLLPIDLER
201  PGKLSFHKHR  AKITNHQNEC  RSCKKWRINI  SFNPMRTIDQ  LNESALITRK
251  RKIFLQEPEI  LQEIKDRTGA  GLKSQVWERF  HRKCFNCRKD  LKLSEVQLDH
301  TRPLAYLWPI  DEHATCLCAQ  CNNTKKDRFP  VDFYSEQQIR  ELSDICGLPY
351  QDLCARSLNL  DQLDRIERNI  AEFSKEWDVR  TFASTARRIS  EVYPARDLFE
401  TLKKESESAY  NKIIEKLKER  PDALLDEALP  LD*
```

FIGURE 12

SEQUENCE LISTING

<160> NUMBER OF SEQ ID NOS: 38

<210> SEQ ID NO 1
<211> LENGTH: 25
<212> TYPE: DNA
<213> ORGANISM: artificial
<220> FEATURE:
<223> OTHER INFORMATION: synthetic

<400> SEQUENCE: 1
gatccgctct cgtcgaccc tcagc                                      25

<210> SEQ ID NO 2
<211> LENGTH: 26
<212> TYPE: DNA
<213> ORGANISM: unknown
<220> FEATURE:
<223> OTHER INFORMATION: primer

<400> SEQUENCE: 2
gatcgctgag ggtcgacgaa gagccg                                    26

<210> SEQ ID NO 3
<211> LENGTH: 31
<212> TYPE: DNA
<213> ORGANISM: unknown
<220> FEATURE:
<223> OTHER INFORMATION: primer

<400> SEQUENCE: 3
agagtcttgc atatgcggag gcttgctaca c                              31

<210> SEQ ID NO 4
<211> LENGTH: 30
<212> TYPE: DNA
<213> ORGANISM: unknown
<220> FEATURE:
<223> OTHER INFORMATION: primer

<400> SEQUENCE: 4
tggtttggat ccctgaaat gggttagggc                                 30

<210> SEQ ID NO 5
<211> LENGTH: 30
<212> TYPE: DNA
<213> ORGANISM: unknown
<220> FEATURE:
<223> OTHER INFORMATION: synthetic

<400> SEQUENCE: 5
tcgaccctca ctacgttagt tcgcatctgc                                30

<210> SEQ ID NO 6
<211> LENGTH: 24
<212> TYPE: DNA
<213> ORGANISM: unknown
<220> FEATURE:
<223> OTHER INFORMATION: synthetic

<400> SEQUENCE: 6
gcagatgcga actaacgtag gggt                                      24

<210> SEQ ID NO 7
<211> LENGTH: 30
<212> TYPE: DNA

```
<213> ORGANISM: unknown
<220> FEATURE:
<223> OTHER INFORMATION: primer

<400> SEQUENCE: 7
gggagatctc gatcccgcga aattaatacg                              30

<210> SEQ ID NO 8
<211> LENGTH: 20
<212> TYPE: DNA
<213> ORGANISM: unknown
<220> FEATURE:
<223> OTHER INFORMATION: primer

<400> SEQUENCE: 8
gcagatgcga actaacgtag                                         20

<210> SEQ ID NO 9
<211> LENGTH: 34
<212> TYPE: DNA
<213> ORGANISM: unknown
<220> FEATURE:
<223> OTHER INFORMATION: primer

<400> SEQUENCE: 9 gggggggcgga gcctatggaa aaacgccagc aacg                        34

<210> SEQ ID NO 10
<211> LENGTH: 24
<212> TYPE: DNA
<213> ORGANISM: unknown
<220> FEATURE:
<223> OTHER INFORMATION: primer

<400> SEQUENCE: 10
cgccagggtt ttcccagtca cgac                                    24

<210> SEQ ID NO 11
<211> LENGTH: 12
<212> TYPE: DNA
<213> ORGANISM: unknown
<220> FEATURE:
<223> OTHER INFORMATION: primer

<400> SEQUENCE: 11
gctcttccgc ta                                                 12

<210> SEQ ID NO 12
<211> LENGTH: 68
<212> TYPE: DNA
<213> ORGANISM: unknown
<220> FEATURE:
<223> OTHER INFORMATION: primer
<220> FEATURE:
<221> NAME/KEY: misc_feature
<222> LOCATION: (51)..(53)
<223> OTHER INFORMATION: n=equal mixture of a,c,g,t

<400> SEQUENCE: 12
gcgggatccg ttcagtccag tggtagtgct tcatcgagaa gtgcgtctgg nnnttccttc    60
aacttctc                                                            68

<210> SEQ ID NO 13
<211> LENGTH: 30
<212> TYPE: DNA
<213> ORGANISM: unknown
<220> FEATURE:
```

```
<223> OTHER INFORMATION: synthetic

<400> SEQUENCE: 13
tcgaccctca ctacgttagt tcgcatctgc                                    30

<210> SEQ ID NO 14
<211> LENGTH: 33
<212> TYPE: DNA
<213> ORGANISM: unknown
<220> FEATURE:
<223> OTHER INFORMATION: primer

<400> SEQUENCE: 14
gcacttatca cacgtaagcg aaagatattc ctg                                 33

<210> SEQ ID NO 15
<211> LENGTH: 33
<212> TYPE: DNA
<213> ORGANISM: unknown
<220> FEATURE:
<223> OTHER INFORMATION: primer

<400> SEQUENCE: 15
caggaatatc tttcgcttac gtgtgataag tgc                                 33

<210> SEQ ID NO 16
<211> LENGTH: 26
<212> TYPE: DNA
<213> ORGANISM: unknown
<220> FEATURE:
<223> OTHER INFORMATION: synthetic

<400> SEQUENCE: 16
ggatccgctc ttcgtcgacc ctcagc                                        26

<210> SEQ ID NO 17
<211> LENGTH: 15
<212> TYPE: DNA
<213> ORGANISM: unknown
<220> FEATURE:
<223> OTHER INFORMATION: synthetic

<400> SEQUENCE: 17
gctcttcgtc gaccc                                                    15

<210> SEQ ID NO 18
<211> LENGTH: 30
<212> TYPE: DNA
<213> ORGANISM: unknown
<220> FEATURE:
<223> OTHER INFORMATION: synthetic

<400> SEQUENCE: 18
tcgaccctca ctacgttagt tcgcatctgc                                    30

<210> SEQ ID NO 19
<211> LENGTH: 29
<212> TYPE: DNA
<213> ORGANISM: unknown
<220> FEATURE:
<223> OTHER INFORMATION: synthetic

<400> SEQUENCE: 19
tgcgtattgg gcgctcttcc gcttcctcg                                     29

<210> SEQ ID NO 20
```

-continued

```
<211> LENGTH: 29
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (24)..(24)
<223> OTHER INFORMATION: nucleotide added by polymerase
<220> FEATURE:
<221> NAME/KEY: misc_feature
<222> LOCATION: (25)..(29)
<223> OTHER INFORMATION: n=g,a,c or t

<400> SEQUENCE: 20
tgcgtattgg gcgctcttcc gctannnnn                                  29

<210> SEQ ID NO 21
<211> LENGTH: 24
<212> TYPE: DNA
<213> ORGANISM: unknown
<220> FEATURE:
<223> OTHER INFORMATION: synthetic

<400> SEQUENCE: 21
gggcgctctt ccgcttcctc gctc                                       24

<210> SEQ ID NO 22
<211> LENGTH: 19
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (13)..(13)
<223> OTHER INFORMATION: nucleotide added by polymerase
<220> FEATURE:
<221> NAME/KEY: misc_feature
<222> LOCATION: (14)..(19)
<223> OTHER INFORMATION: n=g,a,c or t

<400> SEQUENCE: 22
gagcgaggaa gcannnnnn                                             19

<210> SEQ ID NO 23
<211> LENGTH: 1299
<212> TYPE: DNA
<213> ORGANISM: Saccharopolyspora sp.
<220> FEATURE:
<221> NAME/KEY: CDS
<222> LOCATION: (1)..(1299)

<400> SEQUENCE: 23 atg cgg agg ctt gct aca caa cga cgc gag gac gcg tac aaa tca aat    48
Met Arg Arg Leu Ala Thr Gln Arg Arg Glu Asp Ala Tyr Lys Ser Asn
1               5                   10                  15 agg gat tat cag acc gtg cac gaa gct cag agc ctt cga gtc aac tcg    96
Arg Asp Tyr Gln Thr Val His Glu Ala Gln Ser Leu Arg Val Asn Ser
            20                  25                  30 acc gat gat gac aac ctg agc ctc ttc ctc ttg aaa gat att tca ccc   144
Thr Asp Asp Asp Asn Leu Ser Leu Phe Leu Leu Lys Asp Ile Ser Pro
        35                  40                  45 cgc gaa gat tct aaa aat att gta gga ttt gga ggc ttc gtc aag ccc   192
Arg Glu Asp Ser Lys Asn Ile Val Gly Phe Gly Gly Phe Val Lys Pro
    50                  55                  60 gaa atc gcc acc acc atg gcg ctt acc tta acg aca gac atc gat aaa   240
Glu Ile Ala Thr Thr Met Ala Leu Thr Leu Thr Thr Asp Ile Asp Lys
65                  70                  75                  80
```

| | | |
|---|---|---|
| caa ata aaa tca gtg ccg tta tcc tcg aat tgg aat cgg atc agc atc<br>Gln Ile Lys Ser Val Pro Leu Ser Ser Asn Trp Asn Arg Ile Ser Ile<br>                    85                        90                  95 | 288 |
| gtt gca aag ttc gcg agc aac ccg tct gtt agc att act ctg gga ttt<br>Val Ala Lys Phe Ala Ser Asn Pro Ser Val Ser Ile Thr Leu Gly Phe<br>                 100                   105                 110 | 336 |
| gat caa acc cca tgg gtc gat ttc tgg ggc atc aat tcg gac gat atc<br>Asp Gln Thr Pro Trp Val Asp Phe Trp Gly Ile Asn Ser Asp Asp Ile<br>               115                   120                 125 | 384 |
| ggc ctt tca ttt gta tcg gac gca gtc cct ctt gaa atg agc atg att<br>Gly Leu Ser Phe Val Ser Asp Ala Val Pro Leu Glu Met Ser Met Ile<br>       130                   135                 140 | 432 |
| gat agc ata cat att gcc ccc gaa aca cta tac ctt gat cac tca agc<br>Asp Ser Ile His Ile Ala Pro Glu Thr Leu Tyr Leu Asp His Ser Ser<br>145                 150                   155                160 | 480 |
| gca tgt ctc ctt gac att gat cca gtg gaa tcg aca cgc ttc aaa aca<br>Ala Cys Leu Leu Asp Ile Asp Pro Val Glu Ser Thr Arg Phe Lys Thr<br>               165                   170                 175 | 528 |
| ggc cat ggt gac cct tta agt ctg aag aaa tgc tca tac tgc ggc cgc<br>Gly His Gly Asp Pro Leu Ser Leu Lys Lys Cys Ser Tyr Cys Gly Arg<br>       180                   185                 190 | 576 |
| ctt ctt cct ata gac ctc gag cgt ccc ggc aag ctg tct ttt cac aaa<br>Leu Leu Pro Ile Asp Leu Glu Arg Pro Gly Lys Leu Ser Phe His Lys<br>               195                   200                 205 | 624 |
| cat cga gcc aaa atc act aat cat cag aac gag tgt cgt tca tgt aag<br>His Arg Ala Lys Ile Thr Asn His Gln Asn Glu Cys Arg Ser Cys Lys<br>       210                   215                 220 | 672 |
| aag tgg cga ata aac aac tcc ttc aat ccg atg cgc acg att gac cag<br>Lys Trp Arg Ile Asn Asn Ser Phe Asn Pro Met Arg Thr Ile Asp Gln<br>225                 230                   235                240 | 720 |
| ctt aac gag tca gca ctt atc aca cgt gag cga aag ata ttc ctg caa<br>Leu Asn Glu Ser Ala Leu Ile Thr Arg Glu Arg Lys Ile Phe Leu Gln<br>               245                   250                 255 | 768 |
| gaa cca gaa att ctt cag gaa att aag gat agg acc ggc gcg gga ctt<br>Glu Pro Glu Ile Leu Gln Glu Ile Lys Asp Arg Thr Gly Ala Gly Leu<br>             260                   265                 270 | 816 |
| aaa agt caa gtg tgg gaa cga ttc cat cgc aag tgc ttc aac tgt aga<br>Lys Ser Gln Val Trp Glu Arg Phe His Arg Lys Cys Phe Asn Cys Arg<br>               275                   280                 285 | 864 |
| aaa gat ctc aaa cta agc gag gtt caa ctg gac cac act cgg ccg ctt<br>Lys Asp Leu Lys Leu Ser Glu Val Gln Leu Asp His Thr Arg Pro Leu<br>       290                   295                 300 | 912 |
| gca tac cta tgg ccg att gat gag cat gcg act tgc ttg tgc gca caa<br>Ala Tyr Leu Trp Pro Ile Asp Glu His Ala Thr Cys Leu Cys Ala Gln<br>305                 310                   315                320 | 960 |
| tgc aac aat acc aaa aaa gac cgc ttt cct gta gat ttc tat agc gaa<br>Cys Asn Asn Thr Lys Lys Asp Arg Phe Pro Val Asp Phe Tyr Ser Glu<br>               325                   330                 335 | 1008 |
| cag cag ata cgc gaa ctg tcg gac att tgc gga ctt ccg tat cag gat<br>Gln Gln Ile Arg Glu Leu Ser Asp Ile Cys Gly Leu Pro Tyr Gln Asp<br>             340                   345                 350 | 1056 |
| cta tgt gct cgc tcg ttg aat tta gat caa ctc gat agg atc gag cgt<br>Leu Cys Ala Arg Ser Leu Asn Leu Asp Gln Leu Asp Arg Ile Glu Arg<br>               355                   360                 365 | 1104 |
| aat atc gca gag ttc tcc aaa gaa tgg gat gta aga act ttc gca tca<br>Asn Ile Ala Glu Phe Ser Lys Glu Trp Asp Val Arg Thr Phe Ala Ser<br>       370                   375                 380 | 1152 |
| acc gcc cgg aga ata tcg gaa gtt tac ccc gcg cga gac cta ttt gaa<br>Thr Ala Arg Arg Ile Ser Glu Val Tyr Pro Ala Arg Asp Leu Phe Glu<br>385                 390                   395                400 | 1200 |

```
act ctt aag aag gaa agc gag tca gcg tac aat aaa att att gag aag     1248
Thr Leu Lys Lys Glu Ser Glu Ser Ala Tyr Asn Lys Ile Ile Glu Lys
            405                 410                 415 ttg aag gaa aga cca gac gca ctt ctc gat gaa gca cta cca ctg gac     1296
Leu Lys Glu Arg Pro Asp Ala Leu Leu Asp Glu Ala Leu Pro Leu Asp
        420                 425                 430 tga                                                                 1299

<210> SEQ ID NO 24
<211> LENGTH: 432
<212> TYPE: PRT
<213> ORGANISM: Saccharopolyspora sp.

<400> SEQUENCE: 24

Met Arg Arg Leu Ala Thr Gln Arg Arg Glu Asp Ala Tyr Lys Ser Asn
1               5                   10                  15

Arg Asp Tyr Gln Thr Val His Glu Ala Gln Ser Leu Arg Val Asn Ser
            20                  25                  30

Thr Asp Asp Asn Leu Ser Leu Phe Leu Leu Lys Asp Ile Ser Pro
        35                  40                  45

Arg Glu Asp Ser Lys Asn Ile Val Gly Phe Gly Gly Phe Val Lys Pro
    50                  55                  60

Glu Ile Ala Thr Thr Met Ala Leu Thr Leu Thr Thr Asp Ile Asp Lys
65              70                  75                  80

Gln Ile Lys Ser Val Pro Leu Ser Ser Asn Trp Asn Arg Ile Ser Ile
            85                  90                  95

Val Ala Lys Phe Ala Ser Asn Pro Ser Val Ser Ile Thr Leu Gly Phe
            100                 105                 110

Asp Gln Thr Pro Trp Val Asp Phe Trp Gly Ile Asn Ser Asp Asp Ile
        115                 120                 125

Gly Leu Ser Phe Val Ser Asp Ala Val Pro Leu Glu Met Ser Met Ile
    130                 135                 140

Asp Ser Ile His Ile Ala Pro Glu Thr Leu Tyr Leu Asp His Ser Ser
145             150                 155                 160

Ala Cys Leu Leu Asp Ile Asp Pro Val Glu Ser Thr Arg Phe Lys Thr
            165                 170                 175

Gly His Gly Asp Pro Leu Ser Leu Lys Lys Cys Ser Tyr Cys Gly Arg
        180                 185                 190

Leu Leu Pro Ile Asp Leu Glu Arg Pro Gly Lys Leu Ser Phe His Lys
    195                 200                 205

His Arg Ala Lys Ile Thr Asn His Gln Asn Glu Cys Arg Ser Cys Lys
    210                 215                 220

Lys Trp Arg Ile Asn Asn Ser Phe Asn Pro Met Arg Thr Ile Asp Gln
225             230                 235                 240

Leu Asn Glu Ser Ala Leu Ile Thr Arg Glu Arg Lys Ile Phe Leu Gln
            245                 250                 255

Glu Pro Glu Ile Leu Gln Glu Ile Lys Asp Arg Thr Gly Ala Gly Leu
        260                 265                 270

Lys Ser Gln Val Trp Glu Arg Phe His Arg Lys Cys Phe Asn Cys Arg
    275                 280                 285

Lys Asp Leu Lys Leu Ser Glu Val Gln Leu Asp His Thr Arg Pro Leu
    290                 295                 300

Ala Tyr Leu Trp Pro Ile Asp Glu His Ala Thr Cys Leu Cys Ala Gln
305             310                 315                 320

Cys Asn Asn Thr Lys Lys Asp Arg Phe Pro Val Asp Phe Tyr Ser Glu
```

|     |     |     |     | 325 |     |     |     | 330 |     |     |     | 335 |     |     |
| --- | --- | --- | --- | --- | --- | --- | --- | --- | --- | --- | --- | --- | --- | --- |

Gln Gln Ile Arg Glu Leu Ser Asp Ile Cys Gly Leu Pro Tyr Gln Asp
      340                 345                 350

Leu Cys Ala Arg Ser Leu Asn Leu Asp Gln Leu Asp Arg Ile Glu Arg
      355                 360                 365

Asn Ile Ala Glu Phe Ser Lys Glu Trp Asp Val Arg Thr Phe Ala Ser
      370                 375                 380

Thr Ala Arg Arg Ile Ser Glu Val Tyr Pro Ala Arg Asp Leu Phe Glu
385                 390                 395                 400

Thr Leu Lys Lys Glu Ser Glu Ser Ala Tyr Asn Lys Ile Ile Glu Lys
            405                 410                 415

Leu Lys Glu Arg Pro Asp Ala Leu Leu Asp Glu Ala Leu Pro Leu Asp
            420                 425                 430

<210> SEQ ID NO 25
<211> LENGTH: 432
<212> TYPE: PRT
<213> ORGANISM: Saccharopolyspora sp.

<400> SEQUENCE: 25

Met Arg Arg Leu Ala Thr Gln Arg Arg Glu Asp Ala Tyr Lys Ser Asn
1               5                   10                  15

Arg Asp Tyr Gln Thr Val His Glu Ala Gln Ser Leu Arg Val Asn Ser
            20                  25                  30

Thr Tyr Asp Asp Asn Leu Ser Leu Phe Leu Leu Lys Asp Ile Ser Pro
        35                  40                  45

Arg Glu Asp Ser Lys Asn Ile Val Gly Phe Gly Phe Val Lys Pro
    50                  55                  60

Glu Ile Ala Thr Thr Met Ala Leu Thr Leu Thr Thr Asp Ile Asp Lys
65                  70                  75                  80

Gln Val Lys Ser Val Pro Leu Ser Ser Asn Trp Asn Arg Ile Ser Ile
            85                  90                  95

Val Ala Lys Phe Ala Ser Asn Pro Ser Val Ser Ile Thr Leu Gly Phe
            100                 105                 110

Asp Gln Thr Pro Trp Val Asp Phe Trp Gly Ile Asn Ser Asp Asp Ile
        115                 120                 125

Gly Leu Ser Phe Val Ser Asp Ala Val Pro Leu Glu Met Ser Met Ile
    130                 135                 140

Asp Ser Ile His Ile Ala Pro Glu Thr Leu Tyr Leu Asp His Ser Ser
145                 150                 155                 160

Ala Cys Leu Leu Asp Ile Asp Leu Val Glu Ser Thr Arg Phe Lys Thr
            165                 170                 175

Gly His Gly Asp Pro Leu Ser Leu Lys Lys Cys Ser Tyr Cys Gly Arg
        180                 185                 190

Leu Leu Pro Ile Asp Leu Glu Arg Pro Gly Lys Leu Ser Phe His Lys
    195                 200                 205

His Arg Ala Lys Ile Thr Asn His Gln Asn Glu Cys Arg Ser Cys Lys
210                 215                 220

Lys Trp Arg Ile Asn Ile Ser Phe Asn Pro Met Arg Thr Ile Asp Gln
225                 230                 235                 240

Leu Asn Glu Ser Ala Leu Ile Thr Arg Glu Arg Lys Ile Phe Leu Gln
            245                 250                 255

Glu Pro Glu Ile Leu Gln Glu Ile Lys Asp Arg Thr Gly Ala Gly Leu
        260                 265                 270

Lys Ser Gln Val Trp Glu Arg Phe His Arg Lys Cys Phe Asn Cys Arg

```
            275                 280                 285
Lys Asp Leu Lys Leu Ser Glu Val Gln Leu Asp His Thr Arg Pro Leu
        290                 295                 300

Ala Tyr Leu Trp Pro Ile Asp Glu His Ala Thr Cys Leu Cys Ala Gln
305                 310                 315                 320

Cys Asn Asn Thr Lys Lys Asp Arg Phe Pro Val Asp Phe Tyr Ser Glu
                325                 330                 335

Gln Gln Ile Arg Glu Leu Ser Asp Ile Cys Gly Leu Pro Tyr Gln Asp
            340                 345                 350

Leu Cys Ala Arg Ser Leu Asn Leu Asp Gln Leu Asp Arg Ile Glu Arg
        355                 360                 365

Asn Ile Ala Glu Phe Ser Lys Glu Trp Asp Val Arg Thr Phe Ala Ser
370                 375                 380

Thr Ala Arg Arg Ile Ser Glu Val Tyr Pro Ala Arg Asp Leu Phe Glu
385                 390                 395                 400

Thr Leu Lys Lys Glu Ser Glu Ser Ala Tyr Asn Lys Ile Ile Glu Lys
                405                 410                 415

Leu Lys Glu Ile Pro Asp Ala Leu Leu Asp Glu Ala Leu Pro Leu Asp
            420                 425                 430

<210> SEQ ID NO 26
<211> LENGTH: 432
<212> TYPE: PRT
<213> ORGANISM: unknown
<220> FEATURE:
<223> OTHER INFORMATION: Variant E250K of Saccharopolyspora species

<400> SEQUENCE: 26

Met Arg Arg Leu Ala Thr Gln Arg Arg Glu Asp Ala Tyr Lys Ser Asn
1               5                   10                  15

Arg Asp Tyr Gln Thr Val His Glu Ala Gln Ser Leu Arg Val Asn Ser
            20                  25                  30

Thr Asp Asp Asn Leu Ser Leu Phe Leu Leu Lys Asp Ile Ser Pro
        35                  40                  45

Arg Glu Asp Ser Lys Asn Ile Val Gly Phe Gly Gly Phe Val Lys Pro
50                  55                  60

Glu Ile Ala Thr Thr Met Ala Leu Thr Leu Thr Thr Asp Ile Asp Lys
65                  70                  75                  80

Gln Ile Lys Ser Val Pro Leu Ser Ser Asn Trp Asn Arg Ile Ser Ile
                85                  90                  95

Val Ala Lys Phe Ala Ser Asn Pro Ser Val Ser Ile Thr Leu Gly Phe
            100                 105                 110

Asp Gln Thr Pro Trp Val Asp Phe Trp Gly Ile Asn Ser Asp Asp Ile
        115                 120                 125

Gly Leu Ser Phe Val Ser Asp Ala Val Pro Leu Glu Met Ser Met Ile
130                 135                 140

Asp Ser Ile His Ile Ala Pro Glu Thr Leu Tyr Leu Asp His Ser Ser
145                 150                 155                 160

Ala Cys Leu Leu Asp Ile Asp Pro Val Glu Ser Thr Arg Phe Lys Thr
                165                 170                 175

Gly His Gly Asp Pro Leu Ser Leu Lys Lys Cys Ser Tyr Cys Gly Arg
            180                 185                 190

Leu Leu Pro Ile Asp Leu Glu Arg Pro Gly Lys Leu Ser Phe His Lys
        195                 200                 205

His Arg Ala Lys Ile Thr Asn His Gln Asn Glu Cys Arg Ser Cys Lys
210                 215                 220
```

-continued

```
Lys Trp Arg Ile Asn Ile Ser Phe Asn Pro Met Arg Thr Ile Asp Gln
225                 230                 235                 240

Leu Asn Glu Ser Ala Leu Ile Thr Arg Lys Arg Lys Ile Phe Leu Gln
            245                 250                 255

Glu Pro Glu Ile Leu Gln Glu Ile Lys Asp Arg Thr Gly Ala Gly Leu
            260                 265                 270

Lys Ser Gln Val Trp Glu Arg Phe His Arg Lys Cys Phe Asn Cys Arg
        275                 280                 285

Lys Asp Leu Lys Leu Ser Glu Val Gln Leu Asp His Thr Arg Pro Leu
        290                 295                 300

Ala Tyr Leu Trp Pro Ile Asp Glu His Ala Thr Cys Leu Cys Ala Gln
305                 310                 315                 320

Cys Asn Asn Thr Lys Lys Asp Arg Phe Pro Val Asp Phe Tyr Ser Glu
                325                 330                 335

Gln Gln Ile Arg Glu Leu Ser Asp Ile Cys Gly Leu Pro Tyr Gln Asp
            340                 345                 350

Leu Cys Ala Arg Ser Leu Asn Leu Asp Gln Leu Asp Arg Ile Glu Arg
        355                 360                 365

Asn Ile Ala Glu Phe Ser Lys Glu Trp Asp Val Arg Thr Phe Ala Ser
370                 375                 380

Thr Ala Arg Arg Ile Ser Glu Val Tyr Pro Ala Arg Asp Leu Phe Glu
385                 390                 395                 400

Thr Leu Lys Lys Glu Ser Glu Ser Ala Tyr Asn Lys Ile Ile Glu Lys
                405                 410                 415

Leu Lys Glu Arg Pro Asp Ala Leu Leu Asp Glu Ala Leu Pro Leu Asp
            420                 425                 430

<210> SEQ ID NO 27
<211> LENGTH: 11
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (4)..(8)
<223> OTHER INFORMATION: n=g,a,c or t

<400> SEQUENCE: 27
cgannnnntg c                                                          11

<210> SEQ ID NO 28
<211> LENGTH: 11
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (3)..(6)
<223> OTHER INFORMATION: n=g,a,c or t
<220> FEATURE:
<221> NAME/KEY: misc_feature
<222> LOCATION: (10)..(10)
<223> OTHER INFORMATION: y=c or t

<400> SEQUENCE: 28
acnnnngtay c                                                          11

<210> SEQ ID NO 29
<211> LENGTH: 11
<212> TYPE: DNA
```

```
<213> ORGANISM: unknown
<220> FEATURE:
<223> OTHER INFORMATION: synthetic
<220> FEATURE:
<221> NAME/KEY: misc_feature
<222> LOCATION: (3)..(9)
<223> OTHER INFORMATION: n=g,a,c or t

<400> SEQUENCE: 29
ccnnnnnnng g                                                           11

<210> SEQ ID NO 30
<211> LENGTH: 10
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (6)..(10)
<223> OTHER INFORMATION: n=g,a,c or t

<400> SEQUENCE: 30 gagtcnnnnn                                                             10

<210> SEQ ID NO 31
<211> LENGTH: 24
<212> TYPE: DNA
<213> ORGANISM: unknown
<220> FEATURE:
<223> OTHER INFORMATION: adapter

<400> SEQUENCE: 31
gcagatgcga actaacgtag gggt                                             24

<210> SEQ ID NO 32
<211> LENGTH: 20
<212> TYPE: DNA
<213> ORGANISM: unknown
<220> FEATURE:
<223> OTHER INFORMATION: primer

<400> SEQUENCE: 32
gcagatgcga actaacgtag                                                  20

<210> SEQ ID NO 33
<211> LENGTH: 11
<212> TYPE: DNA
<213> ORGANISM: artificial
<220> FEATURE:
<223> OTHER INFORMATION: primer

<400> SEQUENCE: 33
cgacgaagag c                                                           11

<210> SEQ ID NO 34
<211> LENGTH: 18
<212> TYPE: DNA
<213> ORGANISM: artificial
<220> FEATURE:
<223> OTHER INFORMATION: primer

<400> SEQUENCE: 34
tgagggtcga cgaagagc                                                    18

<210> SEQ ID NO 35
<211> LENGTH: 30
<212> TYPE: DNA
```

```
<213> ORGANISM: artificial
<220> FEATURE:
<223> OTHER INFORMATION: primer

<400> SEQUENCE: 35
tgagcgagga agcggaagag cgcccaatat                                    30

<210> SEQ ID NO 36
<211> LENGTH: 24
<212> TYPE: DNA
<213> ORGANISM: artificial
<220> FEATURE:
<223> OTHER INFORMATION: primer

<400> SEQUENCE: 36
gggcgctctt ccgcttcctc gctc                                          24

<210> SEQ ID NO 37
<211> LENGTH: 24
<212> TYPE: DNA
<213> ORGANISM: artificial
<220> FEATURE:
<223> OTHER INFORMATION: primer

<400> SEQUENCE: 37
acgcataacc cgtcgagaag gcga                                          24

<210> SEQ ID NO 38
<211> LENGTH: 12
<212> TYPE: DNA
<213> ORGANISM: artificial
<220> FEATURE:
<223> OTHER INFORMATION: primer

<400> SEQUENCE: 38
ctcgctcctt cg                                                       12
```

METHOD FOR ENGINEERING STRAND-SPECIFIC NICKING ENDONUCLEASES FROM RESTRICTION ENDONUCLEASES

BACKGROUND OF THE INVENTION

There are over 240 Type II restriction endonucleases with unique specificities discovered so far from bacterial and viral sources that are available for research and diagnostic applications. However, only seven nicking enzymes are commercially available: N.BstNBI, N.AlwI, N.BbvCIA, and N.BbvCIB (New England Biolabs, Inc., Beverly, Mass.); N.Bpu10I (Fermentas Inc., Hanover, Md.); and N.CviQXI (CviNY2A) and N.CviPII (CviNYSI) (Megabase Research Products, Lincoln, Nebr. (see cvienzymes). There are a number of phage encoded nicking enzymes such as the gene II protein (gpII) of bacteriophage f1 that are essential for viral DNA replications. Gene II protein introduces a nick in the (+) strand to initiate rolling circle replication. It is also involved in ligating the displaced (+) strand to generate single-strand phage DNA (Geider et al., J. Biol. Chem. 257:6488-6493 (1982); Higashitani et al., J. Mol. Biol. 237:388-400 (1994)). The gpII protein and exonuclease III can be combined and used to generate single strand DNA for mutagenesis and as a template for new DNA strand synthesis in vitro.

There are three major sources for obtaining sequence-specific DNA nicking enzymes. One source is to screen nicking enzymes from the lysates of *Chlorella* algae viruses, from which N.CviQXI (CviNY2A) and N.CviPII (CviNYSI) were originally found (Zhang Y. et al. *Virology*, 240:366-375 (1998); Xia Y. et al. *Nucl. Acids Res.* 16:9477-9487 (1988)). The second source is from bacteria in which the natural occurring nicking enzymes N.BstNBI and N.BstSEI were discovered (Morgan R. D. et al. *Biol. Chem.* 381:1123-5 (2000); Abdurashitov, et al., *Mol. Biol.* (Mosk) 30:1261-1267 (1996)). The third source to obtain nicking enzymes is by protein engineering from existing Type IIA restriction enzymes.

The following classifications are definitions of the different sub-types of Type II restriction endonucleases (Roberts R. J. et al. *Nucl. Acids Res.* 31:1805-1812 (2003)):

Type IIA restriction endonucleases characteristically have asymmetric DNA recognition sequences. The cleavage position can be within the recognition sequence or outside (downstream) of the recognition sequence. Examples are BsmI (GMTGC 1/−1, top strand cleavage one base downstream of the recognition sequence, bottom strand cleavage within the recognition sequence), AciI (CCGC −3/−1), BssSI (CAC-GAG −5/−1), and SapI (GCTCTTC 1/4). Most importantly, Type IIA includes Type IIG, Type IIH, Type IIS, and Type IIT restriction endonucleases. Consequently, many enzymes fall into more than one sub-type. For example, SapI can be identified as a Type IIA or Type IIS enzyme.

Type IIS restriction endonucleases have asymmetric recognition sequences and cleave DNA outside of their recognition sequences, i.e. cleavage 1 to 20 bases outside of DNA recognition sequence. Examples are BsmAI (GTCTC 1/5), BsmBI (CGTCTC 1/5), FokI (GGATG 9/13), and SapI (GCTCTTC 1/4).

Type IIG restriction endonucleases contain a fusion of endonuclease and methylase domains. Therefore, Type IIG enzymes have both endonuclease and methylase activities and the activities may be stimulated by addition of S-adenosylmethionine. The DNA recognition sequences of Type IIG enzymes could be symmetric or asymmetric. Examples are BpmI (CTGGAG 16/14) and BseRI (GAGGAG 10/8). Type IIG enzymes also may belong to Type IIA or Type IIS.

Type IIH restriction endonucleases contain a genetic organization similar to Type I restriction-modification systems. The recognition sequence can be symmetric or asymmetric. Examples are BcgI (10/12 CGAN$_5$TGC 12/10) (SEQ ID NO:27) and BaeI (10/15 ACN$_4$GTAYC 12/7) (SEQ ID NO:28).

Type IIT restriction endonucleases are heterodimers or tetramers (2× heterodimers). The recognition sequence can be symmetric or asymmetric. Examples are Bpu10I (CCT-NAGC −5/−2), BbvCI (CCTCAGC −5/−2), and BslI (CCN$_7$GG) (SEQ ID NO:29).

It would be desirable to generate a large variety of nicking endonucleases derived from restriction endonucleases with asymmetric recognition sequences of which there are more than 79 Type IIA endonucleases known with unique specificities. (see New England Biolabs, rebase).

Many of these Type IIA restriction-modification systems have been cloned and expressed in heterologous hosts (Rebase). Therefore, the protein sequence of many Type IIA restriction enzymes is known although the mechanism of asymmetric cleavage is understood for only a small number of enzymes in particular, Type IIT. For the remaining Type IIA enzymes (where the enzyme is the product of one open reading frame), the predominant mechanism of cleavage is still unclear.

Rationally designed methods have been applied to certain enzymes in which prior knowledge of the dimerization domain is available so that domain swapping can be achieved. Domain swapping relies on a relatively high amino acid sequence similarity between a targeted variant enzyme and a naturally occurring nicking enzyme. For example, Xu et al. *Proc. Natl. Acad. Sci. USA*, 98:12990-12995 (2001) created the nicking enzyme N.AlwI by domain swapping between AlwI and a homologous, naturally occurring nicking enzyme, N.BstNBI (GAGTCNNNN^N, (SEQ ID NO:30), ^ indicates the nicking position). The engineered enzyme N.AlwI cannot form a homodimer and only nicks the top strand of DNA as a monomer.

Besnier et al. *EMBO Report* 2:782-786 (2001); and Kong et al. U.S. Pat. No. 6,395,523 used site-directed mutagenesis to construct a top strand nicking variant of MlyI relying on a high degree of similarity with the naturally occurring nicking enzyme N.BstNBI.

Stahl F. et al. *Proc. Natl. Acad. Sci. USA*, 93:6175-80 (1996) created a nicking enzyme from the Type II restriction endonuclease EcoRV (where the native enzyme forms homodimers and recognizes the symmetric sequence GAT/ATC). The EcoRV nicking enzyme was produced by combining a subunit with an inactive catalytic site with a second subunit with a deficiency in DNA binding. However, such EcoRV variants are non-specific with respect to which strand is nicked and therefore the application of such mutants in DNA manipulation is very limited. In contrast, Heiter et al. (U.S. patent application 20030100094) and Janulaitis et al. (European Patent No. EP 1176204 A1) inactivated the catalytic center in one subunit of a heterodimeric enzyme, which resulted in a nicking endonuclease. However, this approach is limited to Type IIT enzymes with clearly defined and conserved catalytic sites.

In contrast to the above approaches, Heitman and Model described random mutagenesis of EcoRI restriction endonuclease (Heitman J. and Model P., *EMBO J.* 9:3369-3378 (1990)) to identify residues important for substrate recognition. Without any selection for nicking variants, Heitman et al. fortuitously identified a variant possessing nicking activity (Heitman J. and Model P., *Proteins* 7:185-197 (1990)).

SUMMARY OF THE INVENTION

In an embodiment of the invention, a method for engineering a strand-specific nicking endonuclease is provided that includes the steps of: (a) transforming host cells lacking methylase protection against a restriction endonuclease with a plasmid library containing a randomly mutagenized gene encoding the restriction endonuclease, the plasmids including a sequence site outside the gene that is cleavable by an endonuclease encoded by the gene; and (b) culturing the transformants, isolating plasmids therefrom and optionally performing an in vitro selection to identify which plasmids have nicked DNA. The method further comprises cleaving the plasmids with a predetermined strand-specific nicking endonuclease. The nicking site for this endonuclease is a different sequence from that of the randomly mutagenized restriction endonuclease cleavage site. If the nicking endonuclease cleaves on the opposite strand from the mutagenized restriction endonuclease, two cohesive ends result. A reverse primer that is complementary to the cohesive end adjacent to the gene or is identical to all or part of the cohesive end is used for amplifying the gene, together with a forward primer upstream of the gene. The amplified product is then cloned. Alternatively, a selectable marker gene can be inserted between the two cohesive ends of the plasmid, which is then transformed into a host cell and identified in selective medium. The engineered nicking endonuclease is thus obtained by either of the above-described approaches.

The nicking enzyme may nick one or more of a DNA duplex, an RNA/DNA hybrid and an RNA duplex. The host cells may be selected from any bacteria that are known in the art for use in recombinant restriction endonuclease expression. Suitable promoters are selected to obtain desired expression levels. The plasmid library may contain single plasmids or may contain a plurality of different plasmids. Each plasmid may contain a single randomly mutagenized restriction endonuclease gene or may include more than one gene encoding a plurality of enzymes or subunits.

Embodiments of the method include mutagenizing a restriction endonuclease gene to form a deletion, an insertion or a substitution of one or more nucleotides. In particular, the mutagenized gene may have a single mutation or a plurality of mutations. The mutagenized gene may have a deletion in the range of 3 to 600 nucleotides.

In an embodiment of the invention, the method includes selecting or inserting a restriction endonuclease cleavage sequence site downstream from the gene in the plasmid. After the host cells containing the plasmid library have been cultured, the transformants are pooled and plasmids obtained from the pool are analyzed to determine single-strand specificity of a nicking endonuclease encoded by the plasmids. The efficiency of obtaining nicking endonucleases can be enhanced by an enrichment step in which a plasmid DNA preparation from pooled transformants is analyzed after separation of nicked DNA from supercoiled and linear DNA. This separation means may be agarose gel electrophoresis or density centrifugation. Pre-modified *E. Coli* host cells are then transformed with the nicked plasmid DNA and the plasmids from these transformants or the transformants themselves are then divided into two pools so as to test one pool for determining top-strand cleavage activity and one pool for determining bottom-strand cleavage activity.

Determining the strandedness of the nicking endonuclease cleavage activity may be achieved by ligating a single-strand adaptor to the predefined cohesive end. The cohesive end to which an adaptor is attached is formed when the second predetermined cleavage site is located on a top strand in the plasmid and the expressed nicking endonuclease nicks the bottom strand. Similarly, when the second predetermined cleavage site is located on the bottom strand of the plasmid, an expressed nicking endonuclease that nicks the top strand can be detected.

The DNA corresponding to the gene encoding the nicking endonuclease with the defined single-strand nicking activity may be amplified using primers hybridizing to sequences on either side of the gene, for example, at a sequence upstream of the gene and to the single-stranded adaptor or where the primer downstream of the gene is substantially identical in sequence to part of the single-stranded adaptor.

In an embodiment of the invention, a preferred mutation in the nicking endonuclease, determined by sequencing an engineered nicking endonuclease according to a method described above can be introduced by site-directed mutagenesis into an isochizomer or neoschisomer of the restriction endonuclease so as to create a nicking endonuclease. Similarly, the nicking activity of an engineered nicking endonuclease can be enhanced or double-stranded DNA cleavage activity minimized or both by site-directed mutagenesis of a preferred additional mutation.

In an embodiment of the invention, a method is provided wherein the mutagenized restriction endonuclease gene is a Type IIA endonuclease gene. The nicking endonuclease may be a thermostable nicking endonuclease.

In an embodiment of the invention, a method is provided for engineering a strand-specific nicking endonuclease that includes: transforming host cells with plasmids containing randomly mutagenized restriction endonuclease genes, the host cells lacking protective methylation; ligating a single-stranded adaptor to pooled plasmids obtained from surviving transformants for determining which plasmids encode top strand or bottom strand variants of the restriction endonuclease; amplifying the mutagenized restriction endonuclease gene for transforming host cells; determining which host cells have nicking activity and their nicking phenotype; and obtaining the strand-specific engineered nicking endonuclease.

In an embodiment of the method the restriction endonuclease is SapI where the resulting isolated engineered nicking endonucleases are Nt.SapI and Nb.SapI.

In an embodiment of the invention, a method is provided for introducing one or more site-specific nicks into pre-selected strands of a DNA duplex, the method comprising digesting the DNA duplex with a nicking endonuclease under conditions permitting nicking activity.

BRIEF DESCRIPTION OF THE DRAWINGS

FIG. 2 shows an outline of the amplification strategy for selection of bottom strand-specific SapI nicking enzyme clones. The steps include: (a) Ligating adapter to 4-base overhang; (b) using Klenow fill-in reaction; (c) removing unligated adapter using a Spin column; (d) PCR amplification; (e) cloning amplification product into pSAPV6; (f) transforming T7 expression strain protected by SapI methylation; and (g) assaying extracts for nicking activity.

FIG. 6 shows run-off sequencing to confirm the nicking site of Nb.SapI (variant 33). The substrate pUC19 was nicked by a purified lot of variant 33. The nicked circular DNA product was gel-purified and sequenced using primers that converge on the SapI site. Taq DNA polymerase adds an adenine (A) base at the end of the primer extension product (template-independent DNA transferase activity).

FIG. 10 shows the nucleotide sequence (SEQ ID NO:23) and the corresponding amino acid sequence (SEQ ID NO:24) of the wild-type sapIR gene from a *Saccharopolyspora* species.

FIG. 11 shows the amino acid sequence of Nb.SapI (variant 33) (SEQ ID NO:25).

FIG. 12 shows the amino acid sequence of Nt.SapI (variant E250K) (SEQ ID NO:26).

DETAILED DESCRIPTION OF THE INVENTION

Figure 1:
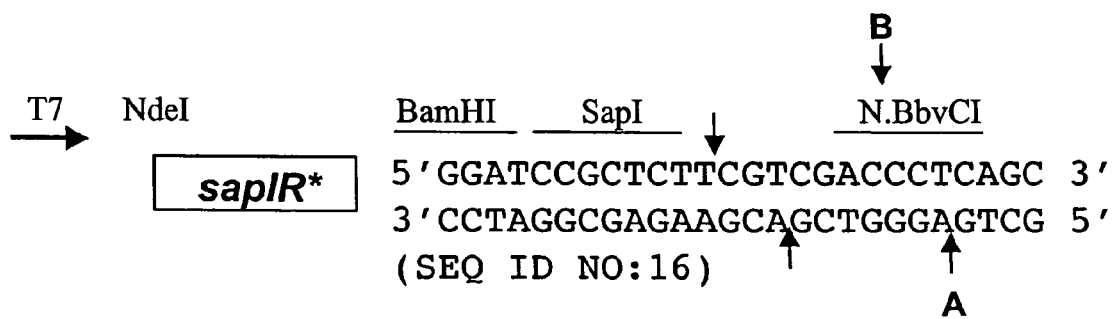
FIG. 1 shows the polylinker sequence of the expression vector pSAPV6 used for selection of SapI nicking enzyme clones. The steps include: (a) preparing randomly mutated SapI endonuclease library in pSAPV6, which is pACYCT7-ter with a modified polylinker; (b) transforming *E. coli* strain where constitutive expression of the wild-type SapI clone results in cell death; (c) pooling surviving colonies and preparing plasmid DNA; (d) fractionating plasmid library by agarose gel electrophoresis and isolating nicked plasmids; (e) dividing plasmid pool into 2 lots and digesting with N.BbvCI A or B to linearize SapI nicked plasmids and creating specific overhangs; (f) ligating single-stranded adapter to overhang; and (g) proceeding with top- or bottom-specific amplification strategy.

Present embodiments of the invention allow a skilled artisan to engineer sequence-specific and top or bottom strand-specific DNA nicking enzymes from existing Type IIA restriction endonucleases with asymmetric recognition sequences.

The method includes making a plasmid library such that plasmids in the plasmid library contain one or more randomly mutagenized restriction endonuclease genes where the gene or genes encode enzymes or subunits. The library may optionally include a mixture of plasmid types and/or a plurality of mutagenized restriction endonucleases which are randomly mutated.

Bacteria are transformed with the plasmid library and a stringent genetic selection occurs in vivo in which restriction endonuclease-expressing plasmids are lethal to host cells when introduced into a strain devoid of cognate methylation protection and where the appropriate level of expression is allowed.

The genetic selection may be followed by one or more in vitro selections to arrive at a final plasmid library where the nicking enzyme clone of interest is enriched and, therefore, easily isolated by limited screening of the library. The genetic selection takes advantage of the fact that a Type IIA enzyme is toxic to the host cell in the absence of protective methylation.

A stringent genetic selection for nicking endonucleases is possible here because the integrity of the bacterial genome is more likely to be maintained after single-stranded cleavage by a nicking endonuclease compared to double-stranded cleavage by a restriction endonuclease. Consequently, a cell expressing the nicking enzyme is more likely to survive. The surviving cells are pooled and the plasmids are isolated from these cells. The first optional in vitro selection is to fractionate the isolated plasmids by agarose gel electrophoresis or density gradient ultracentrifugation.

Because the plasmids are engineered to possess at least one strategically located substrate site adjacent to the restriction or nicking endonuclease, those plasmid clones expressing nicking enzymes may be nicked. The migration of nicked DNA through agarose is significantly retarded as compared to the un-nicked supercoiled form. Alternatively, using density gradient ultracentrifugation (cesium chloride), nicked plasmid and supercoiled plasmid will migrate to different positions after several hours of centrifugation. The separation of nicked from supercoiled plasmids results in the first in vitro plasmid library enrichment step.

After the plasmid DNA corresponding to the nicked, open-circle form is isolated, a second endonuclease is used to digest the DNA in vitro. The second endonuclease may be a nicking enzyme or a restriction enzyme and this substrate site is strategically located adjacent to the first nicking site (the substrate site of interest).

Preferably, the in vitro endonuclease cleavage reaction linearizes the plasmid DNA and creates a pre-defined cohesive end that serves as a handle. The final in vitro step utilizes this pre-defined cohesive end to specifically select those DNA clones expressing either top strand or bottom strand nicking enzyme variants. When the cohesive end is too short in length as a substrate for primer dependent amplification (less than about 4 nucleotides), an adaptor may be attached. The DNA is then amplified by any of the available amplification techniques such as polymerase chain reaction (PCR), helicase-dependent amplification (HDA) or strand-dependent amplification (SDA). Final library members are transformed into bacteria pre-modified by protective methylation and the nicking enzyme is over-expressed so that the cell extract can be assayed for nicking activity. When a nicking variant is isolated, the strand and sequence specificity are confirmed and the entire DNA sequence of the clone is determined. The amino acid substitutions present in each variant are functionally analyzed by determining their impact on nicking endonuclease specificity and nicking activity.

When necessary, a variant is optimized by testing other substitutions at the positions deemed critical for the nicking phenotype. The amino acid substitutions resulting in nicking activity for an endonuclease can be introduced into an isoschizomer, a neoschizomer or an enzyme with a related recognition sequence and a similar amino acid sequence.

The appropriate level of library gene expression is simply optimized by conducting a preliminary study using the wild-type endonuclease clone.

Particular embodiments of the method are provided using SapI (see Examples). The Type IIS restriction endonuclease, SapI, was modified to create strand-specific nicking endonucleases. A SapI variant that predominantly nicks the bottom strand was isolated and designated Nb.SapI variant 33. Moreover, several SapI variants were isolated that exclusively nick the top strand. The most active top strand variant was determined by comparison and was found to contain the amino acid substitution E250K and was designated Nt.SapI.

Embodiments of the method for engineering novel nicking endonucleases include one or more of the following steps:

1. Modification of an Expression Vector (Plasmid)

An appropriate expression vector is selected according to the frequency of cutting sites of the restriction endonuclease to be modified in the bacterial genome. For example, for a restriction endonuclease that is a frequent cutter, it may be desirable to select a vector with a reduced copy number and/or a relatively weak promoter because a nicking endonuclease variant that is a product of randomized mutagenesis may otherwise give rise to toxic effects resulting from large numbers of nicks. For example, a vector with a T7 promoter may be used within a host lacking a T7 RNA polymerase. In the latter scenario, a minimal level of expression is expected from read-through transcription from other promoters present within the vector. Notwithstanding, it may be desirable to vary the vector/host combination to provide enhanced expression. In Example 2, the expression of SapI from a T7 promoter in a non-T7 host was not sufficient for the genetic selection step. Hence, the vector including a T7 promoter was expressed in a host possessing the T7 RNA polymerase.

In addition to a T7 promoter, there are a variety of promoters and plasmids for containing the promoter of choice that are published and/or commercially available. The appropriate plasmid can be selected on the basis of the predicted characteristics of the desired nicking endonuclease to be engineered and its nicking specificity. This can be readily determined without undue experimentation using the assays described for SapI in which the randomly mutated restriction endonuclease is inserted into the selected plasmid for transformation into host cells. The cells can be pooled and assayed for nicked forms and the comparative efficiency of the preliminary steps determined.

Another consideration in vector design is the number and location of substrate sites. In order to maximize the efficiency of the genetic selection step, the vector should not contain substrate sites within the origin of replication or within open reading frames critical for vector function. Likewise, the endonuclease gene of interest should not contain a substrate site subject to nicking by the expressed endonuclease. The presence of substrate sites as described above may interfere with transcription of functional message RNA molecules.

In a preferred embodiment, the appropriate expression vector is modified by insertion of the restriction endonuclease recognition sequence (substrate site) downstream of the gene library cloning sites. (See FIG. 1). This places the DNA substrate at a strategic location within the expression vector and allows for selection of those clones that express endonuclease variants that are able to nick their respective expression vector in vivo.

A second, alternative nicking site may be inserted next to the substrate sequence of interest so that cleavage with a second nicking enzyme will create a double-stranded break with a pre-defined cohesive end. This defined cohesive end thus enables in vitro selection of those mutant endonuclease genes that express site-specific, strand-specific nicking endonucleases. The defined cohesive end may also be produced by double-stranded cleavage adjacent to the nicking site of interest. In this case, a small single-stranded DNA fragment will be produced upon linearization of the expression vector. The short single-stranded DNA (ssDNA) fragment is preferably melted away and separated from the library DNA to avoid interference with further molecular selection steps. Removal of short ssDNA may be accomplished by agarose gel purification or by a spin column procedure as described in Examples 1 and 2.

2. Creation of a Mutant Endonuclease Library

A mutant endonuclease library is created by one of the methods known in the art. For example, mutagenesis of the endonuclease gene may be accomplished by:

(a) Error-prone PCR (Leung, et al., *Technique* 1:11-15 (1989), Cadwell and Joyce, *PCR Methods Applic.*, 2:28-33 (1992)).

(b) Oligonucleotide directed mutagenesis, preferably the overlap extension PCR mutagenesis method (Morrison and Desrosiers, *Biotechniques* 14:454-457 (1993)).

(c) Assembly PCR. The term "assembly PCR" refers to a process that involves the assembly of a PCR product from a mixture of small DNA fragments. A large number of different PCR reactions occur in parallel in the same vial, with the products of one reaction priming the products of another reaction.

(d) Sexual PCR mutagenesis. The term "sexual PCR mutagenesis" (also known as "DNA shuffling") refers to forced homologous recombination between DNA molecules of different but highly related DNA sequence in vitro, caused by random fragmentation of the DNA molecule based on sequence homology, followed by fixation of the crossover by primer extension in a PCR reaction. (Stemmer, *Proc. Natl. Acad. Sci., USA* 91:10747-10751 (1994)).

(e) Cassette mutagenesis. The term "cassette mutagenesis" refers to any process for replacing a small region of a double-stranded DNA molecule with a synthetic oligonucleotide cassette that differs from the native sequence. The oligonucleotide often contains completely or partially randomized native sequence. (Dorner, et al., *J. Mol. Biol.* 285:1515-1523 (1999)).

(f) Recursive ensemble mutagenesis. The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis (Arkin and Youvan, *Proc. Natl. Acad. Sci., USA* 89:7811-7815 (1992)).

(g) Exponential ensemble mutagenesis. The term "exponential ensemble mutagenesis" refers to a process for generating combinatorial libraries with a high percentage of unique and functional mutants, wherein small groups of residues are randomized in parallel to identify, at each altered position, amino acids which lead to functional proteins (Delegrave and Youvan, *Biotechnology Res.* 11:1548-1552 (1993)) and random and site-directed mutagenesis (Arnold, *Curr. Opin. Biotechnol.* 4:450-455 (1993)).

(h) Chemical mutagen: Hydroxylamine, sodium bisulfite or any other chemical mutagen treatment. (Sambrook, J., et al., Molecular Cloning: A Laboratory Manual, $2^{nd}$ ed. Pub. Cold Spring Harbor Laboratory, Cold Spring Harbor, N.Y., 15.105-15.107 (1989)).

(i) In vivo mutagenesis. The term "in vivo mutagenesis" refers to a process of generating random mutations in any cloned DNA of interest which involves the propagation of the DNA in a strain of *E. coli* that carries mutations in one or more of the DNA repair pathways. These mutator strains have a higher random mutation rate than that of a wild-type strain. Propagating plasmid DNA in one of these strains will generate random mutations within the DNA. (Long-McGie, et al., *Biotechnol. Bioeng.* 68:121-125 (2000)). A non-biased mutagenized endonuclease library may be produced by expressing the cognate methylase during the in vivo mutagenesis step.

(j) Inverse PCR mutagenesis utilizing forward and reverse oligonucleotides annealing within or outside of the gene to be randomly mutated. Localized nucleotide randomization may be accomplished by employing oligonucleotides possessing random or semi-random segments.

3. Cloning the Endonuclease Gene Library into an Expression Vector

If the endonuclease gene library is mutated using for example, any of the methods of (a)-(g), then the mutagenized gene library is cloned into the modified expression vector before transformation into the genetic selection bacterial strain. If a mutagenesis method identified in (h)-(j) is used then the mutagenized plasmid library may be transformed directly into the genetic selection bacterial strain and the cloning step may be bypassed.

The host bacterial strain for the genetic selection is one where constitutive and/or induced expression of the wild-type endonuclease gene results in cell lethality. Most laboratory strains will comply with this requirement. The strain may express the T7 RNA polymerase for expression of the gene library from a T7-specific promoter. However, a lethal level of constitutive expression from a T7 vector may not require the presence of the T7 RNA polymerase.

The surviving colonies are pooled and the plasmid DNA is isolated. Those cells containing functionally active restriction endonucleases do not survive in the absence of methylase protection. The surviving bacterial colonies will harbor endonuclease clones that are deficient in double-stranded DNA cleavage activity. Of these clones, in many cases, only a small percentage will express nicking enzymes while the majority of clones will express inactive enzymes.

4. Analysis of Plasmids in the Surviving Host Cells

The plasmid library is subjected to electrophoresis on a preparative agarose gel and the plasmid DNA corresponding to the nicked, open-circle form is isolated from the gel. Alternatively, density gradient ultracentrifugation may be used to isolate nicked plasmids. In a normal plasmid preparation from *E. coli*, some nicked plasmids are present. Therefore, isolation of nicked library plasmids does not ensure that the respective endonuclease gene will encode a nicking enzyme. However, at this point the selected clones can be analyzed for the expression of nicking enzyme variants. The plasmid library isolated from the genetic selection host may be transformed into a host expressing a protective methylase and individual endonuclease variants may be assayed for activity and specificity without subjecting the plasmid library to any in vitro selection procedures.

Figure 3:
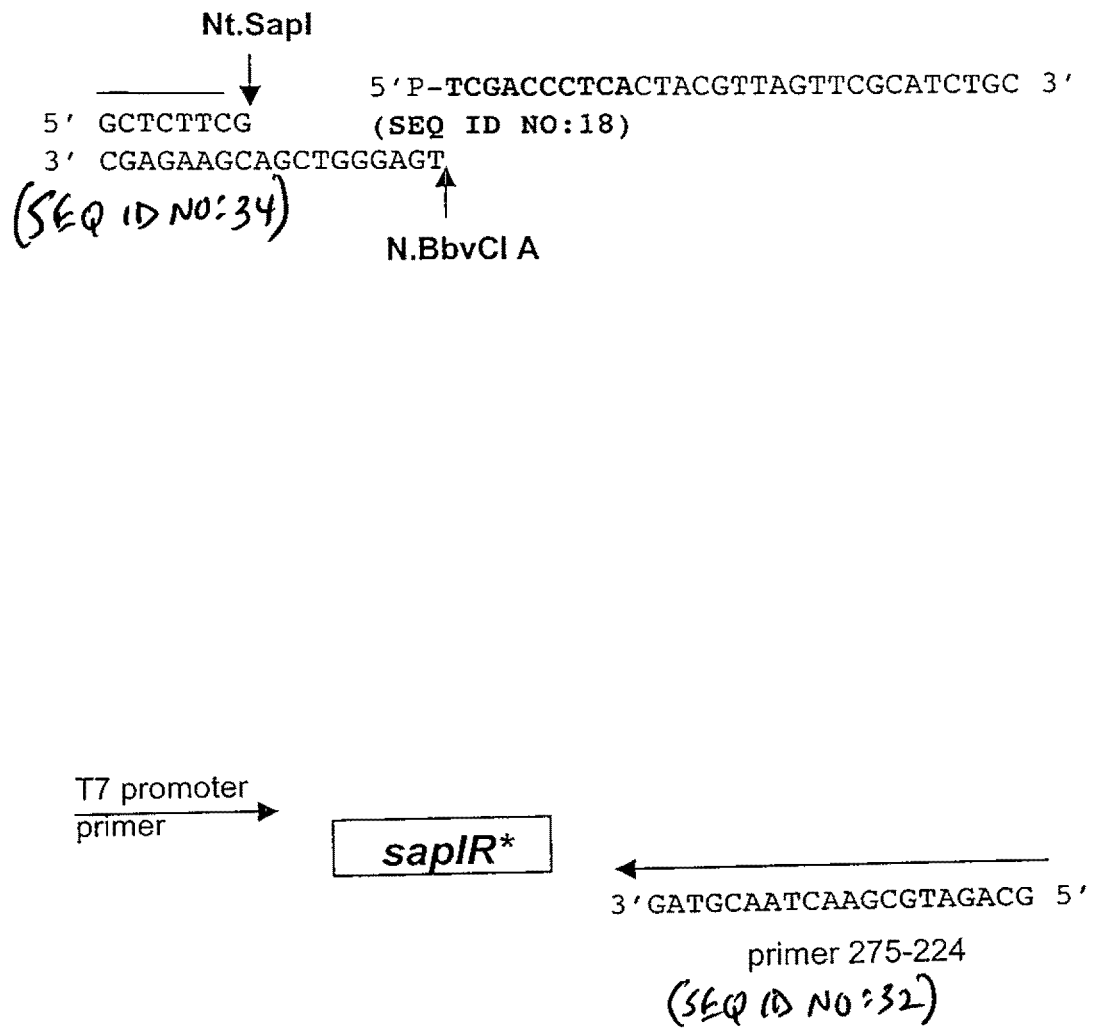
FIG. 3 shows an outline of the amplification strategy for selection of top strand specific SapI nicking enzyme clones.

5. Optional "In vitro" Selection of Plasmid Molecules Encoding Nicking Endonucleases The plasmid library can then be divided into two lots. Subsequent DNA manipulation of each lot is directed to determining strand specificity. Accordingly, top-nicking or bottom-nicking plasmid clones are determined as described below. (FIGS. 2 and 3).

Each lot is digested with the appropriate second nicking enzyme (or restriction enzyme) to linearize the plasmid clones of interest thus creating a pre-defined cohesive end. If a restriction enzyme is used for linearization, then the resulting short ssDNA fragment is removed.

Selection can be achieved by one of several approaches. Some examples of selection methodologies are provided below.

(a) A single-stranded DNA adapter can be ligated to the cohesive end of the plasmid and the mutant genes of interest are amplified from the library using, for example, PCR. For efficient ligation, the cohesive end should preferably be about 4-10 bases. When ligating adapters to cohesive ends greater than 4 nucleotides, the temperature of the plasmid library should be raised, for example, to 55° C., before adding excess adapter followed by cooling to the ligation temperature. Ligation is conducted and is followed by removal of non-ligated adapter by affinity column purification. In a bottom-strand selection procedure, a fill-in reaction is used to synthesize a DNA strand complementary to the ligated adapter. This newly formed strand is used as the template for PCR amplification of the selected gene library. This fill-in reaction subsequent to ligation of the adaptor may be performed, for example, by Klenow fragment. In both top- and bottom-strand selections, nicking enzyme genes of interest can be amplified by PCR. The forward PCR primer should anneal upstream of the endonuclease gene. The reverse PCR primer is designed to be either complementary to the adapter (top selection, FIG. 3) or a truncated version of the adapter (bottom selection, FIG. 2). To minimize false amplification, the 3' end of the reverse primer sequence should preferably not exhibit significant commonality with any region of the expression vector or endonuclease gene. The amplified gene library is cloned back into an expression vector, transformed into a pre-modified host (expressing a cognate or non-cognate DNA methylase) and individual colonies are grown and assayed for expression of the nicking enzyme of interest.

(b) Where the plasmid molecules have pre-defined cohesive ends, an antibiotic resistance gene with the same two cohesive ends may be added as a selection marker to the linearized plasmid library. T4 DNA ligase is added for 10 minutes to 16 hours and the mixture is transformed into bacteria pre-modified with a protective DNA methyltransferase. The transformation mix is plated on media containing the antibiotic corresponding to the inserted resistance gene. The resistant colonies are individually grown and assayed for expression of the nicking enzyme of interest.

(c) If the plasmid library contains plasmids with a site-specific, strand-specific nick generated in vivo and is incubated with a second, alternative nicking enzyme to create a double-strand break, linearized plasmids of interest may be isolated from nicked plasmids by agarose gel electrophoresis. T4 DNA ligase may then be added to the linearized DNA at a low concentration (2-4 ng/μL) to circularize each plasmid. The ligation mix is transformed into a pre-modified host and individual colonies are grown and assayed for expression of the nicking enzyme of interest.

6. Detection of Nicking Enzymes

Nicking enzymes may be detected by assaying cell extract produced from induced or non-induced cultures. Selected library clones are transformed into a pre-modified host strain and cultured with appropriate antibiotics for plasmid selection. Protein expression may be induced at late-log phase. Cell cultures are centrifuged and cell extract is produced by sonication of cells resuspended in a buffer which does not interfere with enzyme activity and aids in maintaining the protein in solution (for example, Tris-HCl or phosphate buffer containing 10 mM β-mercaptoethanol and 0.1 mM EDTA). Alternatively, lysis can be performed by lysozyme treatment, detergent treatment, or freeze-thawing. A typical assay consists of 2-5 μL of cell extract added to 1 μg substrate DNA in a reaction buffer optimal for the wild-type endonuclease. The substrate DNA may contain one or more nicking sites and the mobility of the nicked form must be easily distinguished from the supercoiled form when subjected to agarose gel electrophoresis (i.e. small, high-copy number plasmids such as pUC19 are preferred). The site- and strand-specificity of each nicking variant is determined by run-off sequencing of the nicked DNA product. Each double-stranded plasmid template is sequenced with two primers that converge on the presumed nicking site. If the nicking enzyme is strand-specific, one sequencing reaction will terminate at the nicking site. When Taq DNA polymerase is used for dideoxy terminator sequencing, an adenine (A) base is added at the end of the primer extension product via template-independent DNA transferase activity.

7. Identification of a Mutation in the Endonuclease

The mutant clones of interest are sequenced to determine the corresponding amino acid substitution(s). If more than one amino acid substitution is present, then the responsible substitution(s) is confirmed by site-directed mutagenesis.

8. Optimization of Nicking Enzyme Activity

Optimization of nicking enzyme activity may be carried out by site-directed mutagenesis of the amino acid residues identified in step 7. In some cases, variants with DNA nicking activity also show weak double-stranded DNA cleavage. In order to optimize the nicking activity, the identified amino acid residue may be subjected to site-directed saturation mutagenesis to isolate the remaining amino acid substitutions (for example, 18 mutations). The DNA nicking activity is then compared among all the mutants. The best nicking variant with minimal double-stranded DNA cleavage activity is then selected. Variants containing different amino acid substitutions at the same position may be isolated that display optimal nicking enzyme activity. Amino acid residues affecting nicking activity may be separated or combined to create a superior nicking enzyme. The amino acid substitutions resulting in nicking activity can be introduced into an isoschizomer, a neoschizomer or an enzyme with a related recognition sequence or a similar amino acid sequence (15% to 99% amino acid sequence similarity).

9. Purification of Site-Specific Nicking Endonuclease

To facilitate protein purification, a protein (peptide) tag such as a His tag, chitin-binding domain or maltose-binding domain can be added to the N- or C-terminus of the nicking enzyme. Upon purification, the tag can be removed by protease treatment or protein splicing.

10. Host Organisms for Screening Enzyme Variants

The bacterial host for screening nicking enzyme variants is not limited to *E. coli*. Other bacterial hosts such as *Bacillus* and *Pseudomonas* can also be used provided there are appropriate cloning/expression vectors available and a reasonable efficiency of DNA transformation or electroporation. For thermophilic enzymes, the *Thermus thermophilus* host and *Thermus-E. coli* shuttle vector can be used (Wayne et al. *Gene* 195:321-328 (1997)). This genetic screen method to isolate nicking enzymes can be applied to other DNA cleaving enzymes such as phage terminase, transposase, recombinase, integrase, intron-encoded endonuclease or intein-encoded endonuclease.

This protein engineering method described above can be applied to Type IIA enzymes to obtain top-strand or bottom-strand nicking endonucleases. In the examples, the Type IIS restriction endonuclease SapI was modified to form a SapI variant that predominantly nicks the bottom strand designated as Nb.SapI variant 33. Moreover, several SapI variants were isolated that exclusively nick the top strand. The most active top strand variant contained the amino acid substitution E250K and was designated Nt.SapI (E250K).

There are multiple applications for nicking endonucleases. These include:

1) Strand displacement DNA amplification. A specific nick can be introduced in the target DNA by a nicking enzyme. Bst DNA polymerase or other DNA polymerases can initiate a new strand synthesis at the nick and displace the nicked strand, resulting in linear DNA amplification products.
2) Recombinant DNA technology for gene fragment assembly. Staggered nicks can be introduced in top and bottom strands to generate large cohesive ends (8 to 20 nt long). The complementary cohesive ends can anneal together and bypass the ligation step and the annealed DNA can be used directly in transformation, electroporation, or transfection. Nicking enzymes can also be used in preparation of ssDNA ends for DNA fragment assembly in linear or circular form. Strand-specific DNA nicking enzymes are used to form the single-stranded regions by nicking at the boundaries of the single-stranded regions, either on opposing DNA strands (creating terminal single-stranded regions) or on the same strand (creating a single-stranded gap) (U.S. Pat. No. 6,660,475).
3) Genetic polymorphism detection. Small PCR fragments can be amplified from genomic DNA. A nick is introduced into the target by a nicking enzyme. After denaturing HPLC, the nicked product can be "read" by mass spectrometry to detect genetic alterations. Nicking enzymes may be used for oncogene mutation detection, bacterial and viral pathogen detections.
4) Specific genome targeting. A nicking enzyme with a long recognition sequence or one conjugated with PNA can target a specific region in a genome.
5) Duplex DNA containing a single nick exhibits altered migration in a gel mobility assay. This characteristic could be used for studying differential base stacking and nearest-neighbor energetics.
6) Preparation of nicked-duplex DNA or gapped DNA for studying DNA mismatch excision repair.

Present embodiments of the invention are further illustrated by the following Examples. The examples are provided to aid in the understanding of the invention and are not construed as a limitation thereof. It is understood that for experienced researchers, minor modifications and variations can

EXAMPLES

Example 1

Engineering Strand-Specific Nicking Enzyme Nb.SapI from SapI Restriction Endonuclease 1. Design and Construction of Expression Vector Containing Strategically Located SapI Site.

The polylinker of expression vector pACYCT7-ter (Xu et al. *Mol. Gen. Genet.* 260:226-231 (1998)) was modified to contain a SapI site. Two complementary phosphorylated oligonucleotides (25 mers) were PAGE-purified, annealed and ligated into the BamHI site of pACYCT7-ter. Proper insertion created one BamHI site followed by the sites for SapI, SalI and BbvCI (see FIG. 1). The modified polylinker was confirmed by sequencing with the T7 universal primer from NEB product #S1248S, New England Biolabs, Inc., Beverly, Mass. The modified vector was named pSAPV6.

```
5' P-GATCCGCTCTTCGTCGACCCTCAGC 3'      (SEQ ID NO: 1)
top of polylinker insert (296-332)

5' P-GATCGCTGAGGGTCGACGAAGAGCG 3'      (SEQ ID NO: 2)
bottom of polylinker insert
(296-333)
```

2. Error-Prone PCR Mutagenesis of the sapIR Gene and Isolation of Mutant Plasmid Libraries.

The sapIR gene (1299 bp) was PCR-amplified from the genomic DNA of a *Saccharopolyspora* species (New England Biolabs, Inc., Beverly, Mass.) using 0.4 µM oligonucleotide primers containing NdeI and BamHI sites:

```
5' AGAGTCTTGCATATGCGGAGGCTTGCTAC        (SEQ ID NO: 3)
AC 3' forward (298-022)
```

NdeI site is underlined.

```
5' TGGTTTGGATCCCCTGAAATGGGTTAGGG        (SEQ ID NO: 4)
C 3' reverse (298-023)
```

BamHI site is underlined.

Thermocycling was conducted for 30 cycles (94° C. for 30 sec, 56° C. for 30 sec and 72° C. for 90 sec) in the presence of NEB ThermoPol buffer (New England Biolabs, Inc., Beverly, Mass.) containing 7 mM $MgSO_4$ and five units Taq DNA polymerase. An unequal mixture of dNTPs was added to influence the mutation rate: 0.2 mM dATP, 0.2 mM dGTP, 1.0 mM dCTP and 1.0 mM dTTP. Gene Amp® 2700 (Applied Biosystems, Foster City, Calif.) was used for thermocycling. The PCR product was purified by Qiagen spin column, digested with NdeI and BamHI and then subjected to agarose gel purification. The purified gene library was ligated to pSAPV6 prepared by NdeI/BamHI digestion and CIP treatment. After incubation overnight at 16° C., the ligation mix was heated at 65° C. for 10 min and drop-dialyzed against distilled water for 4 hours. Finally, the ligation mix was transformed into ER1992 cells by electroporation or chemical transformation and plated on LB-agar containing 30 µg/ml chloramphenicol and 80 µg/ml X-gal. ER1992 is a DNA damage indicator strain, which contains the dinD1:lacZ gene fusion (U.S. Pat. No. 5,498,535). When cells are plated on media containing X-gal, the development of blue color indicates induction of the SOS response. An assumption was made that full-strength nicking endonuclease clones might induce the SOS response in *E. coli*. Therefore, 120 medium-blue survivors were pooled in 2 lots. The two 10 ml pools were grown to saturation at 37° C. and plasmid DNA was prepared.

3. In vitro Selection for SaDI Clones that Preferentially Nick Double-Stranded DNA.

Each lot was site-specifically nicked with either N.BbvCIA or N.BbvCIB at 37° C. for 60 min. N.BbvCIA was applied for selection of top nicking SapI clones (FIG. 3) and N.BbvCIB was applied for the selection of bottom nicking SapI clones (FIG. 2). Next the nicking enzymes were removed by Qiagen spin column and adapter ligation reactions were assembled. N.BbvCIA nicked DNA was ligated to 10 pmol phosphorylated adapter 296-334 overnight at 16° C. N.BbvCIB nicked DNA was ligated to 10 pmol adapter 296-335 overnight at 16° C.:

```
5' P-TCGACCCTCACTACGTTAGTTCGCA       (SEQ ID NO: 5)
TCTGC 3' (296-334)

5' GCAGATGCGAACTAACGTAGGGGT 3'        (SEQ ID NO: 6)
(296-335)
```

Klenow fragment (0.5 units) and 30 µM dNTPs were added to the "B ligation" to produce a top DNA strand complementary to the ligated adapter. This step is necessary to create a template for the bottom-specific amplification strategy (FIG. 2). After Klenow fragment fill-in, the polymerase and excess adapter were removed by Qiagen spin column. Finally, "A ligation" and "B ligation" products were PCR-amplified using the same pair of primers (298-024 and 275-224): 5' P-GGGAGATCTCGATCCCGCGAAATTAATACG 3' (298-024) (SEQ ID NO:7) is a forward primer that allows cloning into the SmaI site upstream of the T7 promoter. 5' GCAGATGCGAACTAACGTAG 3' (275-224) (SEQ ID NO:8) is the strategic reverse primer.

PCR amplification was conducted for 33 cycles (94° C. for 30 sec, 56° C. for 30 sec and 72° C. for 90 sec) in the presence of ThermoPol buffer, 0.2 µM each dNTP, 0.4 µM each primer and a Taq/Vent polymerase mixture (5/0.1 units). The expected product of 1493 bp was observed in both A and B templates where adapter had been added during ligation. Templates from mock ligations (where adapter was not added) did not produce the desired PCR product. Additional PCR reactions were conducted for 35 cycles using an annealing temperature of 58° C. to obtain enough product for re-cloning into pSAPV6. PCR products were column purified, digested with BamHI and ligated to pSAPV6 prepared by SmaI/BamHI and CIP treatment. The ligation reactions were transformed into the T7 expression host ER2744 [fhuA2 lacZ::T7 gene1 glnV44 e14-rfbD1? re/A1? endA1 spoT1? thi-1 D(mcrC-mrr)114::IS10] carrying the double methylase clone pBR322-SapIM1M2 (U.S. Pat. No. 5,663,067).

4. Screening Nicking Enzyme Variants from Cell Extracts.

Figure 4:
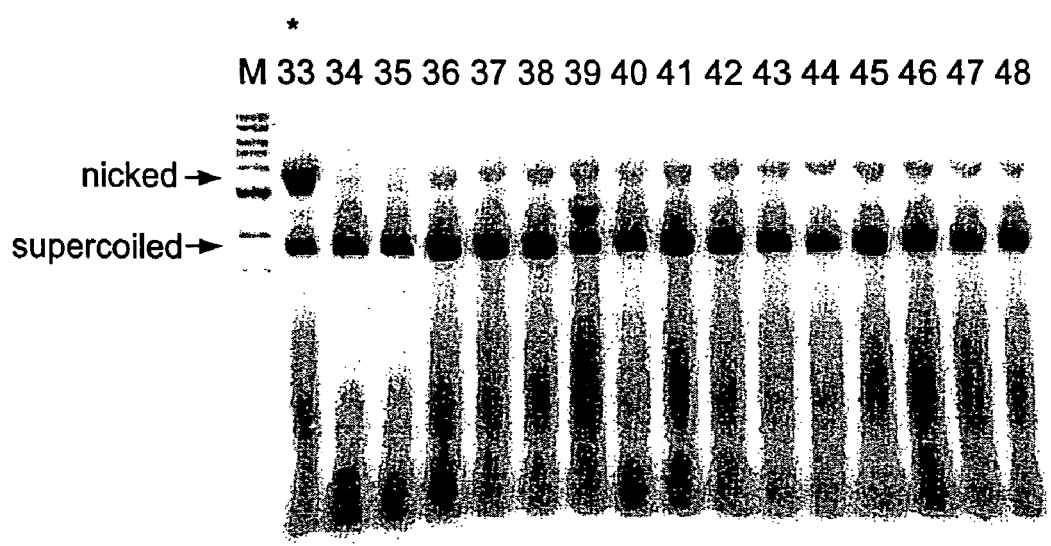
FIG. 4 shows initial isolation of Nb.SapI (variant 33). Nicking activity is revealed by incubating cell extract with supercoiled pUC19. Lane M is a 1 kb DNA ladder where the 3 kb band is prominent. The nicked form of pUC19 migrates at >3 kb. Lane 33 contains a significant level of nicked pUC19 produced by variant 33 extract. Other lanes contain typical levels of nicked pUC19 produced by non-specific nicking activity. Variant 39 displays double-stranded cleavage activity.

Enzyme over-production was accomplished by inoculating single transformants into 10 ml LB containing 30 µg/ml chloramphenicol and 100 µg/ml ampicillin, growing until late-log phase and inducing with 0.1 mM IPTG overnight at 37° C. The cells were pelleted and 1.0 mL cell extract was produced by partial sonication in 10 mM Tris-HCL (pH 7.8), 10 mM β-mercaptoethanol and 0.1 mM EDTA. Nicking activity was assayed by incubating pUC19 (one SapI site) with 3 µL cell extract for 45 min at 37° C. in the presence of 1×NEB buffer 4 (New England Biolabs, Inc., Beverly, Mass.). Of 16 putative bottom-specific clones, one cell extract displayed significant nicking activity (FIG. 4). This clone was initially designated N.33. Of 32 putative top-specific clones, none of the cell extracts displayed nicking activity. Sequencing the sapIR gene of clone N.33 revealed mutations resulting in 4 amino acid substitutions: D34Y/I82V/P168L/R420I.

5. Determination of Strand Specificity for SapI Variant N.33.

The DNA substrate pUC19 was incubated with either N.33 cell extract or partially purified protein. The nicked DNA product was purified from a 1% low-melting agarose gel. The nicked template was identified by sequencing the double-stranded template with two primers that converge on the SapI site: (New England Biolabs, Inc., Beverly, Mass.).

```
                                              (SEQ ID NO: 9)
5' GGGGGGCGGAGCCTATGGAAAAACGCCAGCAACG 3' (266-113)
anneals at pUC origin.
```

```
                                              (SEQ ID NO: 10)
5' CGCCAGGGTTTTCCCAGTCACGAC 3'
(#S1224S) M13/pUC sequencing primer.
```

The sequencing reaction using primer #S1224S terminated at GCTCTTCCGCTA (SEQ ID NO:11) (FIG. 6). This truncated sequence is the product of using a nicked bottom strand as template. Bottom strand nicking occurs between the 4$^{th}$ and 5$^{th}$ nucleotide downstream of the SapI recognition sequence. The final adenine (A) is false as it is added by the terminal transferase activity of Taq DNA polymerase. Upon confirmation of strand specificity, N.33 was re-named Nb.SapI (variant 33).

6. Purification and Characterization of Nb.SapI (Variant 33).

Clone N.33 was transformed into ER2848 [ER2744 with lacI$^q$ on F' (TetR)] pre-modified by pBR322-SapIM1M2. Pre-modification is accomplished by transforming ER2848 with the methylase plasmid and subsequently preparing competent cells by the CaCl$_2$ method. ER2848 [pACYCT7ter-N.33, pBR322-SapIM1M2] was grown at 30° C. to a final volume of 3 liters. Nicking enzyme over-production was induced by the addition of 0.5 mM IPTG during the final 5 hours of growth. The cells were pelleted and frozen at −20° C. The purification procedure was designed according to the purification procedure for wild-type SapI restriction endonuclease. The cell pellet was resuspended by addition of 60 mL HEPES breakage buffer: 20 mM HEPES (pH 7.7), 200 mM NaCl, 1 mM EDTA, 1 mM DTT, 10% glycerol. The cells were lysed by sonication, which was monitored by Bradford assay measurement of released protein. The cell lysate was centrifuged at 15,000 rpm and the clarified lysate was loaded onto a DEAE-Sepharose column pre-equilibrated with HEPES breakage buffer. The flow-through was collected and loaded onto a Heparin-Sepharose FF column pre-equilibrated with HEPES breakage buffer (minus EDTA). Thirty fractions were collected while performing a 0.2-1.0 M NaCl elution gradient. Of these, fractions 3-16 contained significant nicking activity when assayed on pUC19. The active pool was loaded onto a Hydroxyapatite Bio-Gel HTP column pre-equilibrated with HEPES breakage buffer (minus EDTA). A phosphate gradient was employed to elute protein from the Hydroxyapatite resin. Beaker A contained HEPES buffer (minus EDTA) while buffer B contained 0.9 M potassium phosphate (pH 7.7), 200 mM NaCl, 1 mM DTT and 10% glycerol. Twenty-eight fractions were eluted and fractions 9-14 displayed nicking activity. The active pool was subjected to a second DEAE flow-through step to accomplish nucleic acid removal. The second DEAE column was equilibrated with 20 mM HEPES (pH 7.7), 200 mM NaCl, 0.3 mM EDTA, 1 mM DTT and 10% glycerol. The final column was a fractionation on Heparin Sepharose FF using a 0.2-1.0 M NaCl in HEPES breakage buffer (containing 1 mM EDTA). A final pool of 15 mL was dialyzed overnight in SapI storage buffer (minus BSA): 10 mM Tris-HCl (pH7.5), 300 mM, NaCl, 0.1 mM EDTA, 1 mM DTT and 50% glycerol. After dialysis, the volume was reduced to 5.5 mL.

Figure 5:
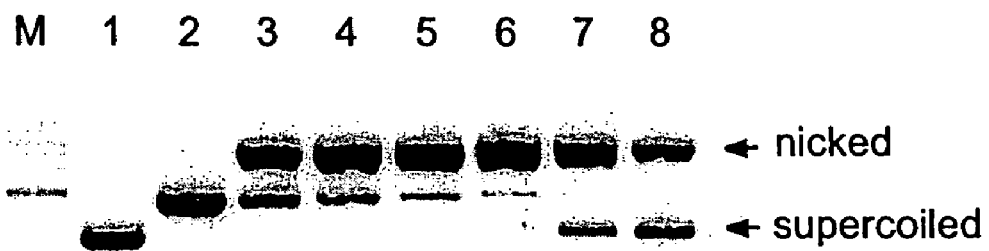
FIG. 5 shows titration of purified Nb.SapI (variant 33) using supercoiled pUC19 as substrate. Lane M is a 1 kb DNA ladder where the 3 kb band is prominent. Lane 1 is uncut pUC19. Lane 2 is pUC19 linearized by SapI. Lanes 3-8 were incubated with 4, 2, 1, 0.5, 0.25, and 0.125 units of Nb.SapI (variant 33) for 60 min at 37° C., respectively.

The purified lot of Nb.SapI (variant 33) was titered in 50 µL reactions containing NEB buffer 4 (New England Biolabs, Inc., Beverly, Mass.), 1 µg pUC19 and 2 µL of diluted enzyme (FIG. 5). The 4-fold dilution of enzyme eliminated all of the supercoiled form of pUC19 after 60 min at 37° C. Therefore, the purified lot of variant 33 contained 2 units/µL. (One unit is defined as the amount of enzyme required to convert 1 µg of pUC19 to open circle form in 60 min at the optimal reaction temperature.)

Upon purification, the strain ER2848 [pACYCT7ter-Nb-.SapI33, pBR322-SapIM1M2] yielded 1100 units of Nb.SapI (variant 33) per gram of cells.

7. Site-Directed Mutagenesis to Analyze the Importance of Individual Amino Acid Substitutions Found in Variant 33.

Positions 34, 168 and 420 were chosen for saturation mutagenesis. Multiple substitutions at position 420 were found to result in enzymes with a preference for nicking pUC19. When assaying variants from cell extract, the following residues at position 420 allowed the most conversion to nicked form: asparagine, serine, threonine. leucine, isoleucine, valine, alanine and glycine.

```
                                              (SEQ ID NO: 12)
5' GCGGGATCCGTTCAGTCCAGTGGTAGTGCTTCATCGAGAAGTGCGT
CTGGNNNTTCCTTCAACTTCTC 3' (300-045)
reverse primer for 420 randomization
N = equal mixture of A,C,G,T
``` reverse primer for 420 randomization
N=equal mixture of A, C, G, T

Molecular Biology Procedures Employed in This Work:

Plasmid DNA preparation procedure: Qiagen spin columns were used to prepare plasmid DNA. Cells lysis, protein and cellular DNA denaturation were performed by addition of P1, P2, and N3 buffers. Clarified supernatant containing Plasmid DNA was loaded onto Qiagen spin columns and washed with PE buffer. Plasmid DNA was eluted with distilled water.

Transformation procedure: Chemically competent cells were prepared by treatment of exponential phase E. coli cells with ice-cold 70 mM CaCl$_2$ for 30 min. Competent cells were mixed with plasmid DNA and incubated on ice for 30 min. After 3-5 min heat treatment at 37° C., an equal amount of LB broth was added and the cells were incubated at 37° C. for one hour. Transformants were plated on LB agar plates with appropriate antibiotics for plasmid selection.

Electroporation procedure: Electro-competent cells were prepared by washing E. coli exponential phase cells in 10% ice-cold glycerol twice (500 mL 10% glycerol for cell pellet from 500 mL cell culture). After mixing the DNA with 50 mL of cells, electroporation was carried out under the condition of 1.8 kV, 200Ω, 25 mF, 0.1 cm cuvette. SOC media (0.5 mL) was added to cells and incubated for 1 hour at 37° C. to amplify the transformants. Transformants were plated on LB agar plates with appropriate antibiotics for plasmid selection.

Run-off sequencing and DNA sequencing: Nicked products or gel-purified nicked products were used for run-off sequencing. Big dye AmpliTaq dideoxy terminator sequencing kit was used in the sequencing reactions (Applied Biosystems, Foster City, Calif.). DNA sequence was resolved on automated sequencer ABI373A. DNA sequence was edited and analyzed with DNASTAR Lasergene programs and GCG programs.

Example 2

Engineering Top Strand-Specific Nicking Enzyme Nt.SapI from SapI Restriction Endonuclease The failure to immediately isolate a top-strand nicking variant was most likely due to the limited size of the initial library (only 120 clones). Furthermore, it was later determined that genetic selection in ER1992 was not stringent enough to adequately eliminate variants with double-stranded cleavage activity. In the case of a rare-cutting enzyme, (i.e SapI) it was advantageous to perform the genetic selection step with a strain encoding the T7 RNA polymerase to increase constitutive SapI expression from pSAPV6.

1. Isolation of Mutant Plasmid Library by Genetic Selection in ER2848.

The same mutagenized sapIR gene described in Example 1 was ligated into pSAPV6 and transformed into ER2848 by electroporation. The transformation mix was plated on LB agar plus Cam and incubated overnight at 30° C. and 37° C. There was no difference in colony number at the two incubation temperatures. Approximately 600 survivors were pooled into 500 ml LB plus Cam. The culture was grown to late-log phase at 37° C., harvested by centrifugation and plasmid DNA was prepared by Qiagen Maxiprep.

2. In Vitro Selection of Nicked Library Plasmids by Agarose Gel Electrophoresis.

A small aliquot (2 of 150 µL) of the ER2848 plasmid library was subjected to agarose gel electrophoresis (0.7% agarose, 150 mV for 90 min). The more slowly migrating DNA was excised from the gel and purified by adsorption to silica (Compass DNA purification kit, American Bioanalytical, Natick, Mass.). This step eliminated most of the supercoiled plasmid DNA and served to enrich the library for nicked plasmid DNA.

3. In Vitro Selection for SapI Clones That Preferentially Nick Double-Stranded DNA on the Top Strand.

The enriched plasmid library was incubated with N.BbvCIA for 60 min at 37° C. to linearize plasmid clones pre-nicked on the top strand of the SapI site in vivo. In such a case, nicking of the bottom strand by N.BbvCIA creates a 10-base cohesive end (FIG. 3). Next, N.BbvCIA was removed by Qiagen spin column and an adapter ligation reaction was assembled. N.BbvCIA nicked DNA was ligated to 10 pmol phosphorylated adapter 296-334 overnight at 16° C. The addition of adapter occurred after heating the nicked DNA to 65° C. to ensure separation of the 10-base cohesive end. T4 DNA ligase (1000 units) was added after cooling to room temperature. A mock ligation without adapter was also assembled.

```
5' P-TCGACCCTCACTACGTTAGTTCGCATC    (SEQ ID NO: 13)
TGC 3' (296-334)
```

After overnight ligation at 16° C., excess adapter was removed by Qiagen spin column. The "A ligation" product was PCR-amplified using primer pair 298-024 and 275-224. The template containing ligated adapter produced a PCR product of the predicted size (1493 bp) while the template from the mock ligation did not produce a product. The "A ligation" products were pooled (400 µL), purified by Qiagen spin column, and digested with NdeI and BamHI. After gel purification, the gene library was ligated into pSAPV6. The ligation reaction was transformed into ER2744 [pBR322-SapM1M2] by electroporation and incubated overnight at 37° C. on LB agar plates containing Amp and Cam.

4. Screening Nicking Enzyme Variants From Cell Extracts.

Figure 7:
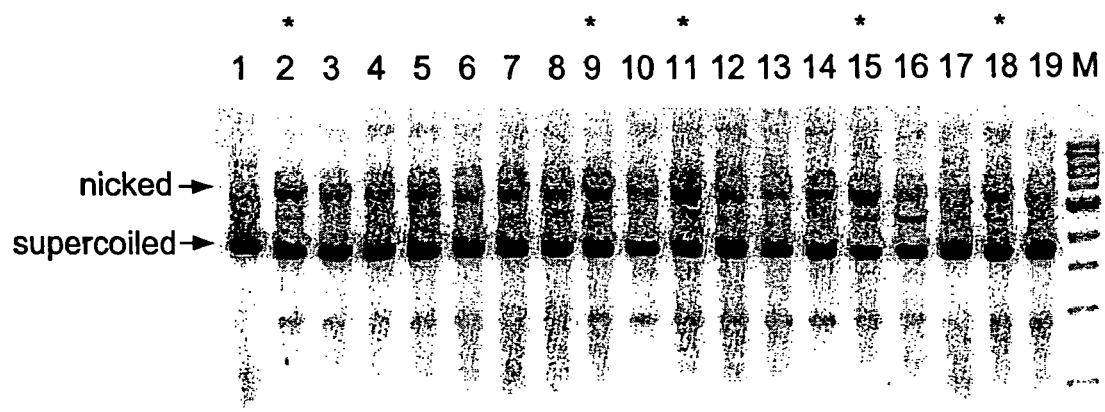
FIG. 7 shows initial isolation of Nt.SapI variants containing the substitution E250K. Nicking activity is revealed by incubating cell extract with supercoiled pUC19. Clones #2, 9, 11, 15 and 18 were sequenced to find that variants 11 and 15 carry the common substitutions K80E, E250K and K273R. Lane M is a 1 kb DNA ladder where the 3 kb band is prominent. The nicked form of pUC19 migrates at >3 kb.

Forty-eight colonies were individually inoculated into 10 ml LB cultures containing Amp and Cam. The cultures were grown at 37° C. until late-log phase and induced overnight with 0.1 mM IPTG. The cultures were centrifuged and the cell pellets were resuspended in 1 mL sonication buffer: 10 mM Tris-HCL (pH 7.8), 10 mM β-mercaptoethanol and 0.1 mM EDTA. Sonication was performed using an Ultrasonics Cell Disruptor. Nicking activity was assayed by incubating pUC19 (one SapI site) with 3 µL cell extract for 60 min at 37° C. in the presence of 1×NEB buffer 4 (New England Biolabs, Inc., Beverly, Mass.). Five of 48 cell extracts were positive for significant nicking activity (FIG. 7). All five clones (#2, #11, #9, #11, #15, #18) were sequenced to determine the responsible amino acid substitutions. The two most active nicking variants (#11 and #15) contained three common substitutions: K80E, E250K and K273R. Site-directed PCR mutagenesis (overlap extension method) was conducted to determine which substitutions(s) were responsible for the nicking phenotype. From these studies, both single variants E250K and K273R produced an exclusively top strand nicked pUC19 product while the variant K80E was negative for nicking activity. In other studies, the variants Q240R and G271R also exhibited exclusive top strand nicking activity when assayed on pUC19. The four top strand nicking variants were named Nt.SapI (E250K), Nt.SapI (K273R), Nt.SapI (Q240R) and Nt.SapI (G271R). Comparative analysis of all top strand nicking variants indicated that substitution E250K results in the most active top strand SapI nicking variant. E250K mutagenesis primers:

```
5' GCACTTATCACACGTAAGCGAAAGATATT    (SEQ ID NO: 14)
CCTG 3' (304-120 forward)

5' CAGGAATATCTTTCGCTTACGTGTGATAA    (SEQ ID NO: 15)
GTGC 3' (304-121 reverse)
```

5. Determination of Strand Specificity for Nt.SapI (E250K).

Figure 9:
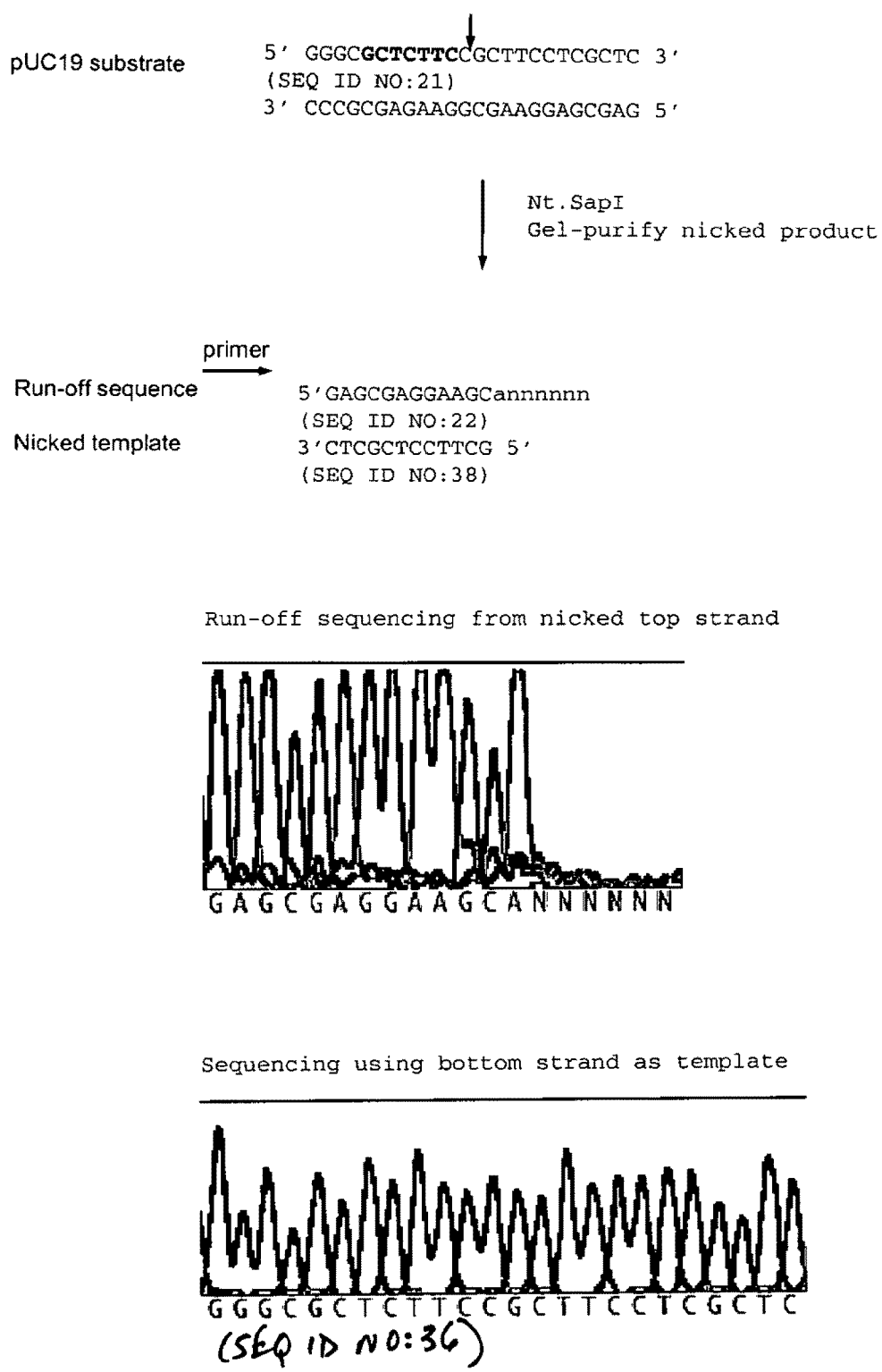
FIG. 9 shows run-off sequencing to determine the nicking site of Nt.SapI (E250K). The substrate pUC19 was nicked by cell extract containing the variant E250K. The nicked circular DNA product was gel-purified and sequenced using primers that converge on the SapI site. Taq DNA polymerase adds an adenine (A) base at the end of DNA (template-independent DNA transferase activity).

The DNA substrate pUC19 (1 µg) was incubated with 5 µL E250K cell extract. The nicked DNA product was purified from a 1% low-melting agarose gel. The nicked template was identified by sequencing the double-stranded template with two primers that converge on the SapI site: (266-113 and New England Biolabs, Inc., Beverly, Mass., catalog #S1224S). The sequencing reaction using primer 266-113 terminated at GGMGCA (FIG. 9). This truncated sequence is the product of using a nicked top strand as template. Top strand nicking occurs between the $1^{st}$ and $2^{nd}$ nucleotide downstream of the SapI recognition sequence. The final adenine (A) is false as it is added by the terminal transferase activity of Taq DNA polymerase.

6. Over-Production of Nt.SapI (E250K).

Figure 8:
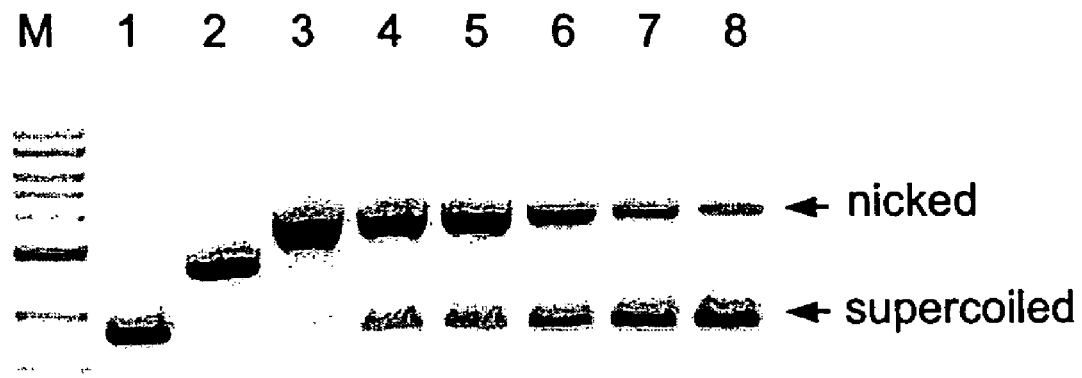
FIG. 8 the activity assay of Nt.SapI (E250K). Nicking activity is revealed by incubating decreasing amounts of cell extract with supercoiled pUC19. Lane M is a 1 kb DNA ladder where the 3 kb band is prominent. Lane 1 is uncut pUC19. Lane 2 is pUC19 linearized by SapI. Lanes 3-8 were incubated with 2, 1, 0.5, 0.25, 0.125 and 0.0625 µL of Nt.SapI for 60 min at 37° C., respectively.

Nt.SapI is over-produced from ER2848 [pACYCT7ter-Nt.SapI, pBR322-SapIM1M2, pSYX33-EarIM1M2] by growing in LB plus Cam/Amp/Kan at 30° C. until late-log phase and then inducing with 0.5 mM IPTG for 5 hrs at 30° C. Cell extract from 10 mL of Nt.SapI (E250K) was titered in 50 µL reactions containing NEB buffer 4 (New England Biolabs, Inc., Beverly, Mass.), 1 µg pUC19 and 2 µL of extract or diluted extract (FIG. 8). The reaction containing 2 µL of undiluted extract eliminated essentially all of the supercoiled form of pUC19 after 60 min at 37° C. Therefore, the production level of Nt.SapI from ER2848 [pACYCT7ter-Nt.SapI, pBR322-SapIM1M2, pSYX33-EarIM1M2] is estimated to be 10,000 units/gram of wet cells.

What is claimed is:

1. A method comprising:
   (a) obtaining a library of plasmids, in which the individual plasmids comprise:
      (i) a gene coding for a wild-type restriction endonuclease that has been randomly mutagenized, and is positioned between a promoter operably linked to the gene and a known asymmetric recognition sequence for the wild-type restriction endonuclease; and
      (ii) a substrate site for nicking by a first nicking endonuclease adjacent to the asymmetric recognition sequence;
   (b) transforming a first population of host cells with the library of plasmids, the first population of host cells lacking a protective methylase for the wild type restriction endonuclease;
   (c) isolating the plasmids from the transformed first population of host cells, the isolated plasmids comprising supercoiled DNAs and open circular DNAs wherein the open circular DNAs contain a nick at the known asymmetric restriction sequence resulting from cleavage by a product of the randomly mutagenized restriction endonuclease gene having nicking activity, the open circular DNAs thus encoding a second nicking endonuclease gene;
   (d) combining the isolated plasmids in vitro with the first nicking endonuclease so as to permit nicking of the isolated plasmids at the substrate site such that the open circular DNAs with the nick at the known asymmetric restriction sequence are linearized; and
   (e) introducing the second nicking endonucleases gene into a second population of host cells premodified with a protective methylase and expressing the second nicking endonucleases gene.

2. The method according to claim 1, wherein the randomly mutagenized restriction endonuclease genes in the library of plasmids differ from the gene encoding the wild-type restriction endonuclease by a deletion, an insertion or a substitution of one or more nucleotides of the wild-type restriction endonuclease gene.

3. The method according to claim 1, further comprising prior to step (d): separating the open circular from the supercoiled plasmid DNA wherein in step (d), the isolated plasmids consist of the open circular DNA.

4. The method according to claim 3, further comprising identifying whether the second nicking endonuclease is:
   (i) a top strand-nicking endonuclease wherein the linearized plasmid is nicked on the bottom strand by the first endonuclease; or
   (ii) a bottom strand-nicking endonuclease wherein the linearized plasmid is nicked on the top strand by the first endonucleases.

5. The method according to claim 1, wherein the linearized DNA in (d) has a 5' cohesive end and a 3' cohesive end and the step of introducing comprises: annealing a DNA adaptor to the 5' cohesive end; selecting a primer for hybridizing to the adaptor or to the 3' cohesive end; amplifying the linearized DNA; and inserting the amplified DNA into a cloning vector such that the amplified DNA is operably linked to an expression control sequence and transformation of the cloning vector into the second population of host cells.

6. The method according to claim 1, wherein the linearized plasmid in (d) has a first cohesive end and a second cohesive end, the step of introducing comprises ligating the first cohesive end to the second cohesive end to form a circular plasmid and transforming the circular plasmid into the second population of host cells pre-modified with the protective methylase.

7. The method according to claim 1, wherein the linearized plasmid in (d) has a first cohesive end and a second cohesive end, the step of introducing comprises: ligating to the first and second cohesive end of the linearized plasmid, a selectable marker gene with the same two cohesive ends; to form a circular plasmid and transforming the circular plasmid into the second population of host cells pre-modified with the protective methylase.

8. The method according to claim 1, wherein step (e) further comprises: over-expressing the second nicking endonuclease in the second population of host cells.

9. The method according to claim 1, further comprising: identifying the one or more mutations in the gene encoding the second nicking endonuclease.

10. The method according to claim 9, further comprising: introducing the one or more mutations into an isoschizomer or neoschizomer of the wild type restriction endonuclease by site-directed mutagenesis.

11. The method according to claim 1, wherein the restriction endonuclease is SapI.

* * * * *